US012672901B2

(12) United States Patent
Biester et al.

(10) Patent No.: US 12,672,901 B2
(45) Date of Patent: Jul. 7, 2026

(54) SEQUENTIAL REDUCER

(71) Applicant: Medos International Sàrl, Le Locle (CH)

(72) Inventors: Eric Biester, Barrington, RI (US); Michael Sorrenti, Middleboro, MA (US); Kevin Yeamans, Raynham, MA (US)

(73) Assignee: Medos International Sàrl, Le Locle (CH)

( * ) Notice: Subject to any disclaimer, the term of this patent is extended or adjusted under 35 U.S.C. 154(b) by 0 days.

(21) Appl. No.: 18/788,075

(22) Filed: Jul. 29, 2024

(65) Prior Publication Data
US 2024/0382240 A1      Nov. 21, 2024

Related U.S. Application Data

(63) Continuation of application No. 17/685,371, filed on Mar. 2, 2022, now Pat. No. 12,053,214.
(Continued)

(51) Int. Cl.
*A61B 17/70*        (2006.01)
*A61B 17/00*        (2006.01)

(52) U.S. Cl.
CPC ...... *A61B 17/7086* (2013.01); *A61B 17/7032* (2013.01); *A61B 17/7082* (2013.01); *A61B 2017/00407* (2013.01)

(58) Field of Classification Search
CPC ............ A61B 17/7086; A61B 17/7076; A61B 17/7085
See application file for complete search history.

(56) References Cited

U.S. PATENT DOCUMENTS 5,443,467 A      8/1995   Biedermann et al.
5,601,446 A      2/1997   Wright
(Continued)

FOREIGN PATENT DOCUMENTS

CN        101052357 A      10/2007
CN        101128158 B      10/2010
(Continued)

OTHER PUBLICATIONS

[NoAuthorListed] Expedium Spine System Surgical Technique Guide, DePuy Spine Inc., 2011, 36 pages.
(Continued)

*Primary Examiner* — Eduardo C Robert
*Assistant Examiner* — Anna V. Little
(74) *Attorney, Agent, or Firm* — Barnes & Thornburg LLP

(57)        ABSTRACT

Surgical instruments that are configured to couple to a bone anchor assembly to provide a modular platform for carrying out various steps of a surgical procedure, such as spinal rod reduction and derotation, are provided. For example, in one embodiment a surgical instrument can include an outer sleeve terminating in a pair of extensions, an inner sleeve having a proximal threaded portion and a distal translating portion configured to pass through the outer sleeve, and a pair of pivoting arms received in the extensions of the outer sleeve. The pivoting arms can be configured to extend into a channel of the outer sleeve to couple a bone anchor to the outer sleeve, and a proximal end portion of the outer sleeve can include one or more flats configured to engage with another instrument.

21 Claims, 30 Drawing Sheets

Related U.S. Application Data

(60) Provisional application No. 63/157,395, filed on Mar. 5, 2021.

(56) References Cited

U.S. PATENT DOCUMENTS

| | | | |
|---|---|---|---|
| 6,736,820 | B2 | 5/2004 | Biedermann et al. |
| 6,974,460 | B2 | 12/2005 | Carbone et al. |
| 7,179,261 | B2 | 2/2007 | Sicvol et al. |
| 7,611,517 | B2 | 11/2009 | Lim |
| 7,618,444 | B2 | 11/2009 | Shluzas |
| 7,887,541 | B2 | 2/2011 | Runco et al. |
| 7,918,858 | B2 | 4/2011 | Stad et al. |
| 8,137,356 | B2 | 3/2012 | Hestad et al. |
| 8,206,395 | B2 | 6/2012 | McLean et al. |
| 8,235,997 | B2 | 8/2012 | Hoffman et al. |
| 8,246,623 | B2 | 8/2012 | Peultier et al. |
| 8,273,089 | B2 | 9/2012 | Jackson |
| 8,303,595 | B2 | 11/2012 | Jones |
| 8,308,774 | B2 | 11/2012 | Hoffman et al. |
| 8,439,924 | B1 | 5/2013 | McBride et al. |
| 8,460,308 | B2 | 6/2013 | Marino et al. |
| 8,540,718 | B2 | 9/2013 | Dauster et al. |
| 8,556,903 | B2 | 10/2013 | Miller et al. |
| 8,556,904 | B2 | 10/2013 | Rezach et al. |
| 8,764,756 | B2 | 7/2014 | Jones |
| 8,790,348 | B2 | 7/2014 | Stad et al. |
| 8,845,649 | B2 | 9/2014 | Jackson |
| 8,900,240 | B2 | 12/2014 | White et al. |
| 8,906,062 | B2 | 12/2014 | Nichols et al. |
| 8,961,523 | B2 | 2/2015 | Barrus et al. |
| 8,979,848 | B2 | 3/2015 | Butters et al. |
| 8,986,349 | B1 | 3/2015 | German et al. |
| 9,060,817 | B2 | 6/2015 | Justis |
| 9,066,761 | B2 | 6/2015 | McBride et al. |
| 9,078,709 | B2 | 7/2015 | McBride |
| 9,149,307 | B2 | 10/2015 | Sandstrom et al. |
| 9,186,188 | B2 | 11/2015 | Gleason et al. |
| 9,204,909 | B2 | 12/2015 | Rezach et al. |
| 9,220,539 | B2 | 12/2015 | McBride et al. |
| 9,220,543 | B2 | 12/2015 | Walker et al. |
| 9,241,743 | B2 | 1/2016 | Hopkins et al. |
| 9,247,969 | B2 | 2/2016 | Nunley et al. |
| 9,265,533 | B2 | 2/2016 | Nelson et al. |
| 9,271,768 | B2 | 3/2016 | Artaki et al. |
| 9,452,000 | B2 | 9/2016 | Barrus |
| 9,468,474 | B2 | 10/2016 | Parikh et al. |
| 9,486,256 | B1 | 11/2016 | Lish et al. |
| 9,517,099 | B2 | 12/2016 | Bess et al. |
| 9,743,962 | B2 | 8/2017 | Viart et al. |
| 9,833,268 | B2 | 12/2017 | Walker |
| 9,844,400 | B2 | 12/2017 | Stevenson et al. |
| 9,901,378 | B2 | 2/2018 | Dauster et al. |
| 9,918,752 | B2 | 3/2018 | Hennard et al. |
| 9,918,753 | B2 | 3/2018 | May et al. |
| 9,943,343 | B2 | 4/2018 | Meyer et al. |
| 9,962,197 | B2 | 5/2018 | Dandaniopoulos et al. |
| 10,028,771 | B2 | 7/2018 | Artaki et al. |
| 10,039,578 | B2 | 8/2018 | Anderson et al. |
| 10,064,662 | B2 | 9/2018 | Gunn et al. |
| 10,085,778 | B2 | 10/2018 | Semingson et al. |
| 10,117,678 | B2 | 11/2018 | Angus |
| 10,136,927 | B1 | 11/2018 | Lish et al. |
| 10,154,862 | B2 | 12/2018 | Miller et al. |
| 10,166,050 | B2 | 1/2019 | Heuer |
| 10,299,839 | B2 | 5/2019 | Sicvol et al. |
| 10,398,481 | B2 | 9/2019 | Goel et al. |
| 10,405,896 | B2 | 9/2019 | Noordeen et al. |
| 10,433,884 | B2 | 10/2019 | Barrett et al. |
| 10,524,843 | B2 | 1/2020 | Mladenov et al. |
| 10,568,669 | B2 | 2/2020 | Reitblat et al. |
| 10,610,269 | B2 | 4/2020 | Mickiewicz et al. |
| 10,675,066 | B2 | 6/2020 | George |
| 10,682,167 | B2 | 6/2020 | Sandstrom et al. |
| 10,702,315 | B2 | 7/2020 | Lindner |
| 10,709,477 | B2 | 7/2020 | Manninen et al. |
| 10,716,602 | B2 | 7/2020 | Fischer |
| 10,729,477 | B2 | 8/2020 | Cain et al. |
| 10,772,663 | B2 | 9/2020 | Harper |
| 10,898,241 | B2 | 1/2021 | Lish et al. |
| 11,426,215 | B2 | 8/2022 | Rezach et al. |
| 11,439,441 | B2 | 9/2022 | Mickiewicz et al. |
| 11,478,284 | B2 | 10/2022 | Vazifehdan et al. |
| 11,484,349 | B2 | 11/2022 | Peultier et al. |
| 11,553,947 | B2 | 1/2023 | Park et al. |
| 11,660,128 | B2 | 5/2023 | Lish et al. |
| 11,684,397 | B2 | 6/2023 | Barrus |
| 11,717,331 | B2 | 8/2023 | Rezach et al. |
| 11,730,522 | B2 | 8/2023 | Avidano et al. |
| 11,730,523 | B2 | 8/2023 | Stoll et al. |
| 11,911,080 | B2 | 2/2024 | George |
| 12,042,188 | B2 | 7/2024 | Rezach et al. |
| 12,053,213 | B2 | 8/2024 | Mickiewicz et al. |
| 12,053,214 | B2 | 8/2024 | Biester et al. |
| 12,133,666 | B2 | 11/2024 | Brooke et al. |
| 12,232,783 | B2 | 2/2025 | Lish et al. |
| 2006/0036255 | A1 | 2/2006 | Pond, Jr. et al. |
| 2006/0074418 | A1 | 4/2006 | Jackson |
| 2006/0074445 | A1 | 4/2006 | Gerber et al. |
| 2006/0111730 | A1 | 5/2006 | Hay |
| 2007/0093817 | A1 | 4/2007 | Barrus et al. |
| 2007/0191841 | A1 | 8/2007 | Justis et al. |
| 2007/0213714 | A1 | 9/2007 | Justis |
| 2008/0015601 | A1 | 1/2008 | Castro et al. |
| 2008/0045955 | A1 | 2/2008 | Berrevoets et al. |
| 2008/0077138 | A1 | 3/2008 | Cohen et al. |
| 2008/0228233 | A1 | 9/2008 | Hoffman et al. |
| 2009/0157125 | A1 | 6/2009 | Hoffman et al. |
| 2009/0228055 | A1 | 9/2009 | Jackson |
| 2010/0114174 | A1 | 5/2010 | Jones et al. |
| 2010/0121385 | A1 | 5/2010 | Blain et al. |
| 2011/0077690 | A1 | 3/2011 | Shin et al. |
| 2011/0118791 | A1 | 5/2011 | Nunley et al. |
| 2011/0257692 | A1 | 10/2011 | Sandstrom et al. |
| 2011/0263945 | A1 | 10/2011 | Peterson et al. |
| 2011/0288599 | A1 | 11/2011 | Michielli et al. |
| 2012/0191144 | A1 | 7/2012 | Peultier et al. |
| 2012/0277808 | A1 | 11/2012 | May |
| 2013/0018419 | A1 | 1/2013 | Rezach et al. |
| 2013/0053901 | A1 | 2/2013 | Cormier et al. |
| 2013/0090697 | A1 | 4/2013 | George |
| 2013/0096618 | A1 | 4/2013 | Chandanson et al. |
| 2013/0103039 | A1 | 4/2013 | Hopkins et al. |
| 2013/0103094 | A1 | 4/2013 | Beale et al. |
| 2013/0238030 | A1 | 9/2013 | Steib |
| 2013/0317558 | A1 | 11/2013 | Varieur et al. |
| 2014/0052197 | A1 | 2/2014 | McBride et al. |
| 2014/0074106 | A1 | 3/2014 | Shin |
| 2014/0142585 | A1 | 5/2014 | Rutledge |
| 2014/0148865 | A1* | 5/2014 | Hennard ............ A61B 17/7086 606/86 A |
| 2014/0180298 | A1 | 6/2014 | Stevenson et al. |
| 2014/0276894 | A1 | 9/2014 | Ramsay et al. |
| 2014/0276896 | A1 | 9/2014 | Harper |
| 2014/0277167 | A1 | 9/2014 | Hutton et al. |
| 2014/0277170 | A1 | 9/2014 | Barrett et al. |
| 2014/0277206 | A1 | 9/2014 | Reitblat et al. |
| 2014/0311264 | A1 | 10/2014 | Black et al. |
| 2014/0316475 | A1 | 10/2014 | Parikh et al. |
| 2015/0039035 | A1 | 2/2015 | Krüger |
| 2015/0066042 | A1 | 3/2015 | Cummins et al. |
| 2015/0066089 | A1 | 3/2015 | Nelson et al. |
| 2015/0100098 | A1 | 4/2015 | Moore |
| 2015/0112397 | A1 | 4/2015 | Petit |
| 2015/0148849 | A1 | 5/2015 | Abidin |
| 2015/0173807 | A1 | 6/2015 | Artaki et al. |
| 2015/0351810 | A1 | 12/2015 | Lindner et al. |
| 2016/0022317 | A1 | 1/2016 | Kraus |
| 2016/0030093 | A1 | 2/2016 | Walker |
| 2016/0089188 | A1 | 3/2016 | McBride, Jr. et al. |
| 2016/0235450 | A1 | 8/2016 | Walker et al. |
| 2016/0296266 | A1* | 10/2016 | Chandanson ....... B25B 23/0035 |
| 2016/0367296 | A1 | 12/2016 | Walker |
| 2017/0100116 | A1 | 4/2017 | Erramilli et al. |
| 2017/0105773 | A1 | 4/2017 | Barrus et al. |

(56) References Cited

U.S. PATENT DOCUMENTS

| | | | |
|---|---|---|---|
| 2017/0143385 A1 | 5/2017 | Biyani et al. | |
| 2017/0164980 A1 | 6/2017 | Le Roux et al. | |
| 2018/0055545 A1 | 3/2018 | Biedermann et al. | |
| 2018/0116703 A1 | 5/2018 | Schäfer et al. | |
| 2018/0185072 A1 | 7/2018 | Rubin et al. | |
| 2019/0069934 A1* | 3/2019 | Mickiewicz | A61B 17/708 |
| 2019/0117280 A1 | 4/2019 | Avidano et al. | |
| 2019/0183542 A1* | 6/2019 | Lish | A61B 17/7083 |
| 2019/0231400 A1 | 8/2019 | Jackson et al. | |
| 2019/0274740 A1 | 9/2019 | Stoll et al. | |
| 2019/0380748 A1 | 12/2019 | Doose et al. | |
| 2019/0380750 A1 | 12/2019 | Morris | |
| 2020/0093521 A1 | 3/2020 | Klausman et al. | |
| 2020/0205864 A1 | 7/2020 | Mickiewicz et al. | |
| 2020/0305932 A1* | 10/2020 | Park | A61B 17/7091 |
| 2020/0367939 A1 | 11/2020 | Loftis et al. | |
| 2021/0059725 A1* | 3/2021 | Avidano | A61B 17/7086 |
| 2022/0280207 A1 | 9/2022 | Biester et al. | |
| 2022/0354548 A1 | 11/2022 | Mast et al. | |
| 2023/0085069 A1 | 3/2023 | Mickiewicz et al. | |
| 2023/0389967 A1 | 12/2023 | Goel et al. | |
| 2024/0008905 A1 | 1/2024 | Daniels | |
| 2024/0382238 A1 | 11/2024 | Mickiewicz et al. | |
| 2025/0099143 A1 | 3/2025 | Mast et al. | |

FOREIGN PATENT DOCUMENTS

| | | |
|---|---|---|
| CN | 1913836 B | 11/2010 |
| CN | 103648420 A | 3/2014 |
| CN | 110072481 A | 7/2019 |
| DE | 102011103252 A1 | 11/2012 |
| JP | 2008514365 A | 5/2008 |
| JP | 2013524929 A | 6/2013 |
| JP | 2014176705 A | 9/2014 |
| JP | 2020532403 A | 11/2020 |
| WO | 2009152308 A1 | 12/2009 |
| WO | 2009158707 A1 | 12/2009 |
| WO | 2011133160 A1 | 10/2011 |
| WO | 2012103344 A3 | 10/2012 |
| WO | 2015140440 A1 | 9/2015 |
| WO | 2015145343 A1 | 10/2015 |

OTHER PUBLICATIONS

A Solutions for Simple and Complex Spine Pathology MATRIX Spine System Degenerative Surgical Technique (2017) DePuySynthes.

Chinese Office Action for Application No. 201880057651.0, dated Feb. 21, 2023 (19 pages).

European Examination Report for Application No. 18853556.1 dated Jun. 12, 2024 (6 pages).

International Search Report and Written Opinion for Application No. PCT/US18/47130, mailed Nov. 9, 2018 (10 pages).

Extended European Search Report for Application No. 18853556.1, issued May 3, 2021 (7 pages).

Japanese Search Report for Application No. 2020-534162, issued Jun. 6, 2022 (22 pages).

Japanese Notice of Reasons for Refusal for Application No. JP 2023-553684 dated Jul. 1, 2025 (12 pages).

Japanese Decision of Refusal for Application No. JP 2023-553684 dated Oct. 28, 2025 (12 pages).

U.S. Appl. No. 15/695,335, filed Sep. 5, 2017, Modular Surgical Instruments and Related Methods, Medos International Sàrl.

U.S. Appl. No. 16/815,945, filed Mar. 11, 2020, Modular Surgical Instruments and Related Methods, Medos International Sàrl.

U.S. Appl. No. 17/884,531, filed Aug. 9, 2022, Modular Surgical Instruments and Related Methods, Medos International Sàrl.

U.S. Appl. No. 17/685,371, filed Mar. 2, 2022, Sequential Reducer, Medos International Sàrl.

Chinese First Office Action for Application No. 202280019300.7 dated Mar. 2, 2026 (16 pages).

* cited by examiner

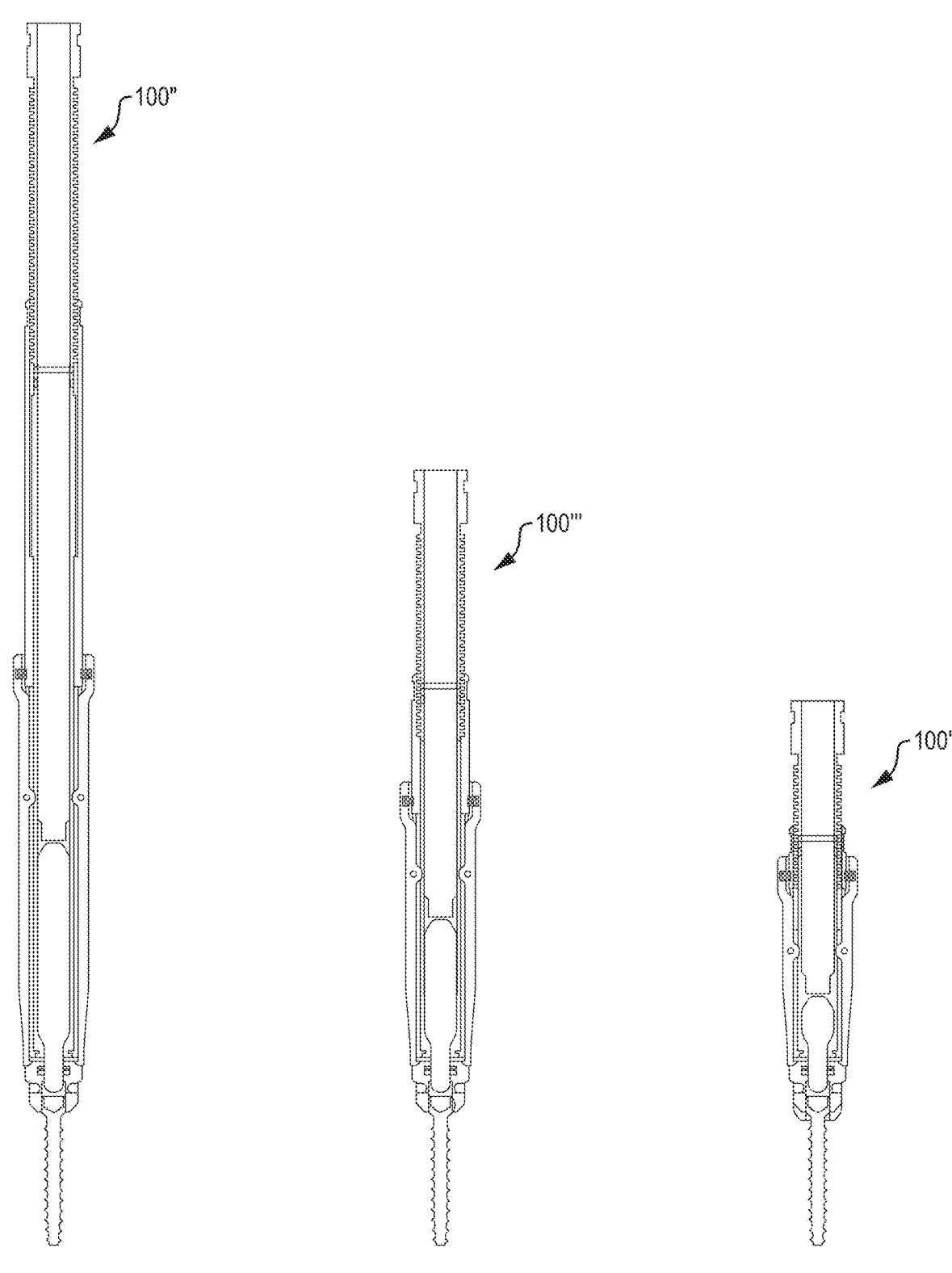
FIG. 9A                    FIG. 9B                    FIG. 9C

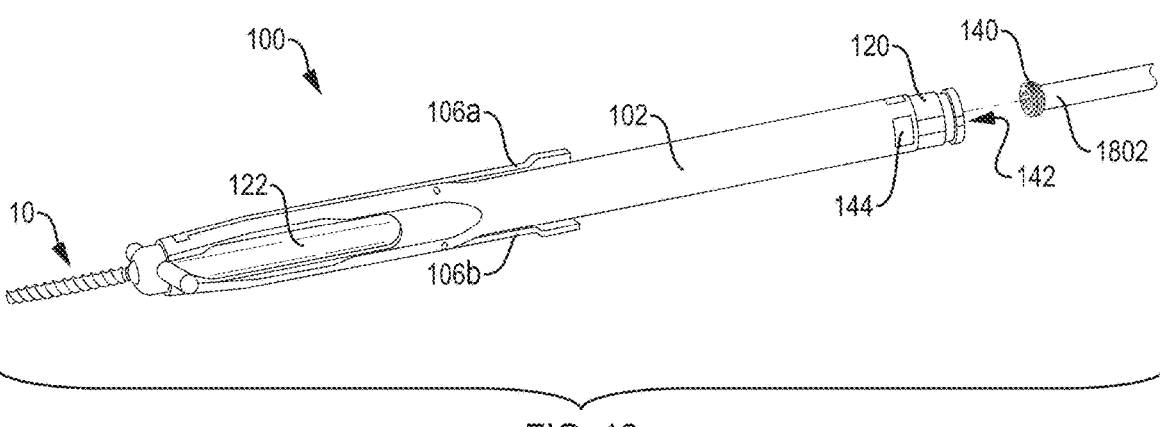
FIG. 18
FIG. 19
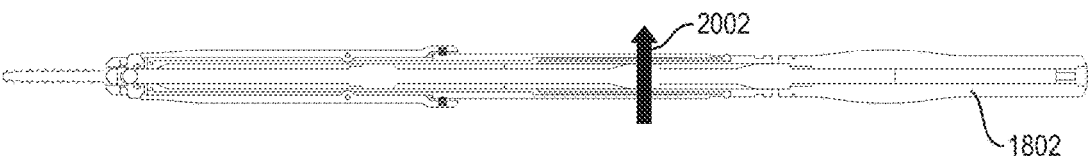
FIG. 20

SEQUENTIAL REDUCER

CROSS-REFERENCE TO RELATED APPLICATIONS

This application is a continuation of U.S. application Ser. No. 17/685,371, filed on Mar. 2, 2022. U.S. application Ser. No. 17/685,371 claims the benefit of U.S. Provisional Application No. 63/157,395, entitled "Sequential Reducer and Modular Derotation Tube," filed on Mar. 5, 2021. The entire contents of each of these application are hereby incorporated by reference herein.

FIELD

This disclosure relates generally to surgical instruments and methods of use and, more particularly, to surgical instruments for performing rod reduction, derotation, and/or set screw insertion during spinal surgery.

BACKGROUND

Fixation systems can be used in orthopedic surgery or neurosurgery to maintain a desired spatial relationship between multiple bones or bone fragments. For example, in spinal surgery, a spinal fixation system can be implanted into a patient to align and/or fix a desired orientation of one or more vertebrae. A typical spinal fixation system can include bone anchors implanted in the vertebrae and longitudinal rods that are secured to the bone anchors by set screws or other closure mechanisms. Implanting the fixation system can involve multiple steps, e.g., rod reduction, derotation, set screw insertion, among others.

Rod reduction, derotation, and set screw management can be a challenging part of posterior spinal fixation procedures. Traditionally, multiple separate instruments have been required to perform these steps. Accordingly, a large number of instruments must be prepared and made available during the surgery, the surgeon must repeatedly switch between several different instruments, and frequent insertion, removal, and re-insertion of instruments to and from the surgical site can be required. All of this can lead to surgeon fatigue, prolonged operating time, and patient risks associated therewith.

Accordingly, there is a need for improved instruments, systems, and methods that can reduce the number of steps and amount of instrumentation required to perform spinal fixation procedures.

SUMMARY

The present disclosure generally relates to various embodiments of rod reducers and derotation sleeves that can address challenges with workflow, usability, and manufacturing of said devices. An example device can include an outer sleeve configured to couple to a bone anchor assembly to provide a modular platform for carrying out various steps of a surgical procedure. For example, the outer sleeve can receive an inner sleeve therethrough for reducing a spinal rod into the bone anchor assembly. The inner sleeve can include a threaded member and a translating member that contacts the rod to drive the rod distally into the bone anchor assembly. A derotation instrument can be attached to the reduction instrument for performing derotation maneuvers or applying other manipulation forces. A modular driver or handle adapter can be attached to the reduction instrument and/or to the derotation instrument to facilitate rod reduction. Any of the instrument body, the reduction instrument, and the derotation instrument can include a working channel therethrough. A set screw or closure mechanism, and a driver instrument for applying the set screw or closure mechanism to the bone anchor assembly, can be inserted through the working channel.

In one aspect, a surgical instrument is disclosed that includes an outer sleeve having an inner channel defined therein, the outer sleeve terminating in a pair of extensions at a distal end thereof. The instrument further includes an inner sleeve having a proximal threaded portion and a distal translating portion configured to pass through the outer sleeve, and a pair of pivoting arms received in the extensions in the outer sleeve. The pivoting arms are configured to extend into the channel to couple a bone anchor to the outer sleeve. Further, a proximal end portion of the outer sleeve includes one or more flats configured to engage with another instrument.

Any of a variety of alternative or additional features can be included and are considered within the scope of the present disclosure. For example, in some embodiments, the pivoting arms can be spring-loaded to bias to a closed position.

In certain embodiments, the threaded portion can include a first threaded portion and a second threaded portion separated by a non-threaded portion.

In some embodiments, the threaded portion can be configured to be pulled and rotated to be removed from the outer sleeve.

In certain embodiments, the proximal end portion of the outer sleeve can include a circumferential groove.

In some embodiments, the pair of pivoting arms can include a nub that extends into one or more longitudinal grooves of the distal translating portion of the inner sleeve to prevent rotation of the distal translating portion relative to the outer sleeve. In other embodiments, the instrument can include a pin that extends into one or more longitudinal grooves of the distal translating portion of the inner sleeve to prevent rotation of the distal translating portion.

In certain embodiments, the instrument can further include a counter-torque device having a mating feature that corresponds to the one or more flats on the outer sleeve.

In some embodiments, the instrument can further include a derotation sleeve that defines a lumen therethrough, the derotation sleeve being configured to couple to the outer sleeve. The derotation sleeve can have one or more engagement surfaces that overlap with the one or more flats to facilitate coupling. In certain embodiments, the derotation sleeve can further include a pair of hinged arms that are configured to extend into the lumen to further couple the derotation sleeve to the outer sleeve. In some embodiments, the derotation sleeve can further include a locking ring configured to selectively constrain movement of the hinged arms. Further, in some embodiments the hinged arms can be received in a circumferential groove along the outer sleeve.

In another aspect, a surgical instrument is disclosed that includes a housing having a central opening, a proximal end, a distal end, and a central longitudinal axis (A1) extending between the proximal and distal ends. The instrument further includes first and second fixed arms extending distally from the housing, as well as first and second pivoting arms movably coupled to the housing. Each pivoting arm can have a proximal end and a distal end, with the pivoting arms being configured to selectively retain a bone anchor therebetween. The instrument further includes a reducer shaft threadably mounted in the central opening of the housing. Further, each of the first and second arms extend distally from the housing to define an inner surface and each of the first and second arms includes sidewalls extending outward from the inner surface at lateral ends of each arm.

As with the instruments described above, any of a variety of additional or alternative features are considered within the scope of the present disclosure. For example, in some embodiments the inner surface of each of the first and second arms can have a conical tapering profile.

In certain embodiments, opposed, inward-facing surfaces of each sidewall of an arm can have a planar tapering profile.

In some embodiments, the pivoting arms can be mounted in recesses formed in the fixed arms.

In certain embodiments, the pivoting arms can be pivotably coupled to the housing at a location intermediate the proximal and distal ends of the pivoting arms.

In some embodiments, the reducer shaft can include a first portion having an exterior thread and being configured to rotate relative to the housing to advance the reducer shaft distally relative to the housing. The reducer shaft can further include a second portion that is rotationally-fixed relative to the housing, the second portion comprising a distal-facing rod-engaging surface. The first portion can include one or more inwardly-facing projections received within a circumferential groove formed in an exterior surface of the second portion.

In certain embodiments, the reducer shaft can define a working channel extending therethrough.

In some embodiments, a distal end portion of the reducer shaft can include a visualization window formed therein.

In certain embodiments, the reducer shaft can include a drive interface at a proximal end of the reducer shaft.

In some embodiments, the reducer shaft can include a handle at a proximal end thereof that is configured to be grasped by a user.

In certain embodiments, the instrument can further include a derotation shaft selectively attachable to the reducer shaft. In some embodiments, the derotation shaft can include an elongate body defining a working channel extending therethrough, the working channel of the derotation shaft being in communication with a working channel of the reducer shaft and the central opening of the housing. In other embodiments, the derotation shaft can include opposed hinged arms and a locking ring. The locking ring can be movable between a locked position, in which the locking ring maintains the hinged arms in a radially inward position where they engage a groove formed in the housing, and an unlocked position, in which the hinged arms can move radially outward to disengage from the groove of the housing.

In some embodiments, the derotation shaft can include a drive interface at a proximal end of the derotation shaft.

In certain embodiments, the sidewalls can include extensions that form a notch between each extension and the inner surface. The notch can be configured to receive a portion of a bone anchor.

In some embodiments, the reducer shaft can include a substantially flat distal surface configured to engage a spinal rod. In other embodiments, the reducer shaft can include a concave distal surface configured to engage a spinal rod.

Any of the features or variations described herein can be applied to any particular aspect or embodiment of the present disclosure in a number of different combinations. The absence of explicit recitation of any particular combination is due solely to avoiding unnecessary length or repetition.

4

BRIEF DESCRIPTION OF THE DRAWINGS

The aspects and embodiments of the present disclosure can be more fully understood from the following detailed description taken in conjunction with the accompanying drawings, in which:

FIG. 9A is a side cross-sectional view of the reducer instrument of FIG. 7 engaging a bone anchor with the inner sleeve disposed at a proximal position;

FIG. 9B is a side cross-sectional view of the reducer instrument of FIG. 8 engaging a bone anchor with the inner sleeve disposed at a proximal position;

FIG. 9C is a side cross-sectional view of the reducer instrument of FIG. 6 engaging a bone anchor with the inner sleeve disposed at a proximal position;

FIG. 18 is a perspective view of a set screw being advanced towards the distally reduced spinal rod of FIG. 17;

FIG. 19 is a perspective side cross-sectional view of a set screw being coupled to a bone anchor through the reducer instrument of FIG. 12;

FIG. 20 is a side cross-sectional view of a derotation maneuver performed on the reducer instrument of FIG. 12;

DETAILED DESCRIPTION

Figure 1:
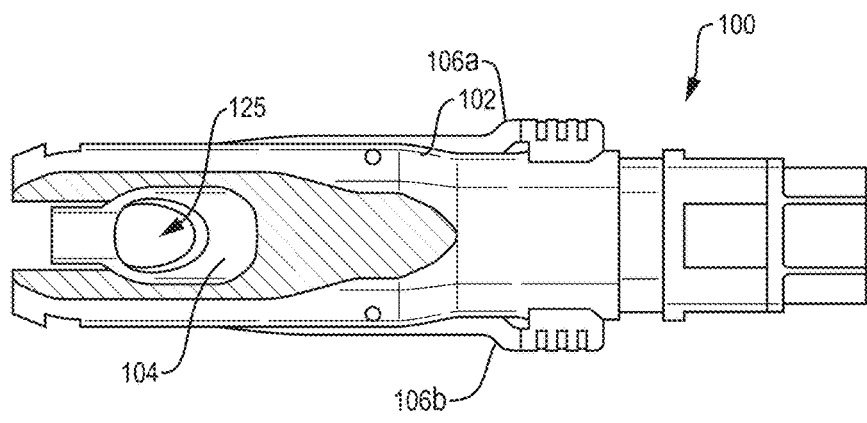
FIG. 1 is a side view of one embodiment of a reducer instrument of the present disclosure.

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure. Additionally, to the extent that linear, circular, or other dimensions are used in the description of the disclosed devices and methods, such dimensions are not intended to limit the types of shapes that can be used in conjunction with such devices and methods. Equivalents to such dimensions can be determined for different geometric shapes, etc. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

Disclosed herein are various embodiments of rod reducers and derotation sleeves that can address challenges with workflow, usability, and manufacturing of said devices. An example device can include an outer sleeve configured to couple to a bone anchor assembly to provide a modular platform for carrying out various steps of a surgical procedure. For example, the outer sleeve can receive an inner sleeve therethrough for reducing a spinal rod into the bone anchor assembly. The inner sleeve can include a threaded member and a translating member that contacts the rod to drive the rod distally into the bone anchor assembly. A derotation instrument can be attached to the reduction instrument for performing derotation maneuvers or applying other manipulation forces. A modular driver or handle adapter can be attached to the reduction instrument and/or to the derotation instrument to facilitate rod reduction. Any of the instrument body, the reduction instrument, and the derotation instrument can include a working channel therethrough. A set screw or closure mechanism, and a driver instrument for applying the set screw or closure mechanism to the bone anchor assembly, can be inserted through the working channel.

The instruments and devices disclosed herein can be used in the same procedures as those described in U.S. Pat. No. 10,610,269, entitled "Modular surgical instruments and related methods," the disclosure of which is hereby incorporated by reference in its entirety. The instruments and devices disclosed herein can be advantageous for certain clinical applications, providing an ability to couple with an implant separately from a rod reduction process. For example, as discussed below, the disclosed instruments and devices can facilitate coupling with an implant construct, either before or after implantation of the construct in a patient. Once positioned relative to a spinal fixation rod or other element, the disclosed instruments and devices can achieve rod reduction through actuation of a threaded mechanism. In some surgical procedures, the disclosed instruments and devices can be operated to couple with an implant construct, reduce a rod into the implant, permit a user to lock the rod into the implant construct, e.g., using a set screw, disengage from the implant construct, and repeat the same or similar operations to reduce the rod into another implant construct.

An indicated above, the disclosed instruments and devices can couple with an implant before a rod reduction process starts. This feature can provide an option to, e.g., lock multiple reducer instruments onto respective implant constructs before effecting a rod reduction process. The reducer instruments can be left free-standing without user input to maintain their position and/or degree of rod reduction, and they can be individually operated to reduce or partially reduce a rod into each of the respective implants, thereby allowing a surgeon to sequentially effect the overall reduction process along a patient's spine without disengaging and reengaging a reducer instrument to different implants. In some embodiments, the reducer instruments can serve to temporarily hold the rod in a desired position until the surgeon is satisfied with the overall reduction process. Once the rod is fully reduced into the implant constructs, the rod can be locked into the respective implant constructs by applying a set screw or other fixation device through a lumen formed in each reducer instrument, as described below.

Figure 2:
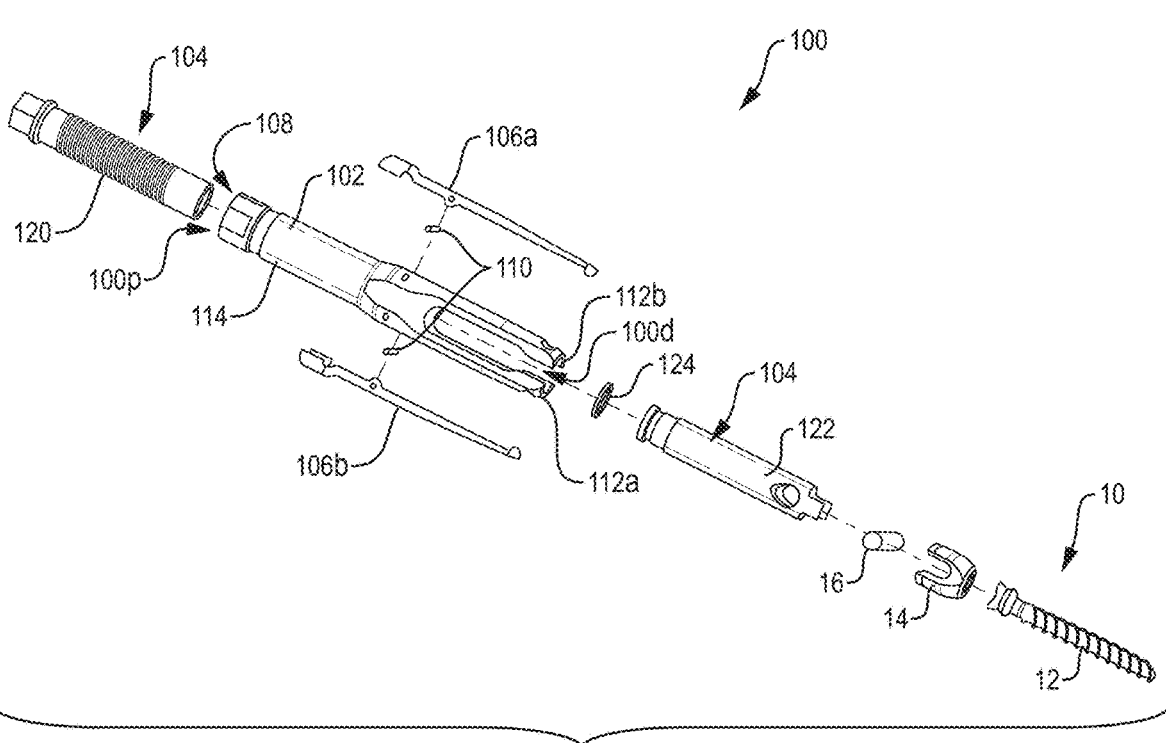
FIG. 2 is an exploded perspective view of the reducer instrument of FIG. 1.

FIGS. 1 and 2 illustrate one embodiment of a reducer instrument 100 of the present disclosure that can be used to provide a platform for various surgical steps, such as rod reduction, derotation, and/or set screw insertion. The reducer instrument 100 can include an outer sleeve 102, an inner sleeve 104, and a pair of pivoting arms 106 attached to the outer sleeve. The outer sleeve 102 can define a working channel 108 configured to receive at least a portion of another tool or instrument, e.g., the inner sleeve 104, therein. The channel 108 can provide access to the surgical site to allow passage of instruments or implants therethrough. The channel 108 can extend from a proximal end 100*p* of the reducer instrument 100 to a distal end 100*d* of the reducer instrument. Pins 110 can couple the arms 106 to the outer sleeve 102.

Figure 3:
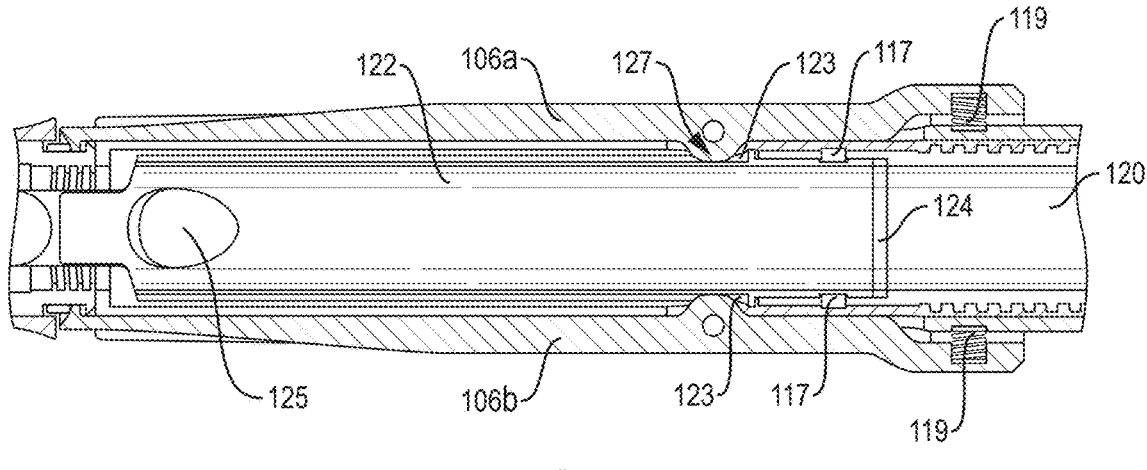
FIG. 3 is a side cross-sectional detail view of the reducer instrument of FIG. 1.
Figure 6:
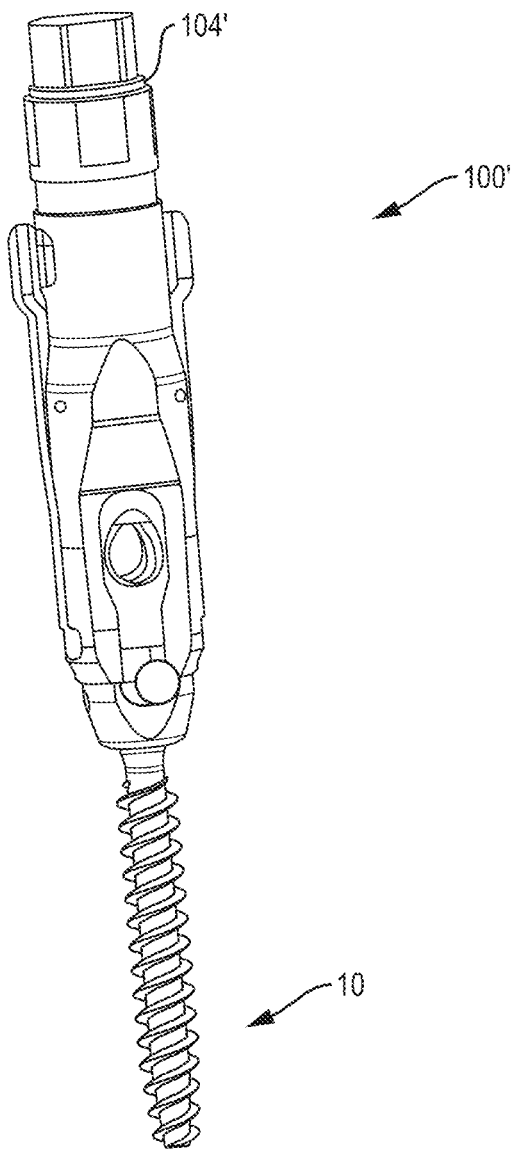
FIG. 6 is a perspective view of one embodiment of a reducer instrument of the present disclosure coupled to a bone anchor and spinal fixation rod.
Figure 7:
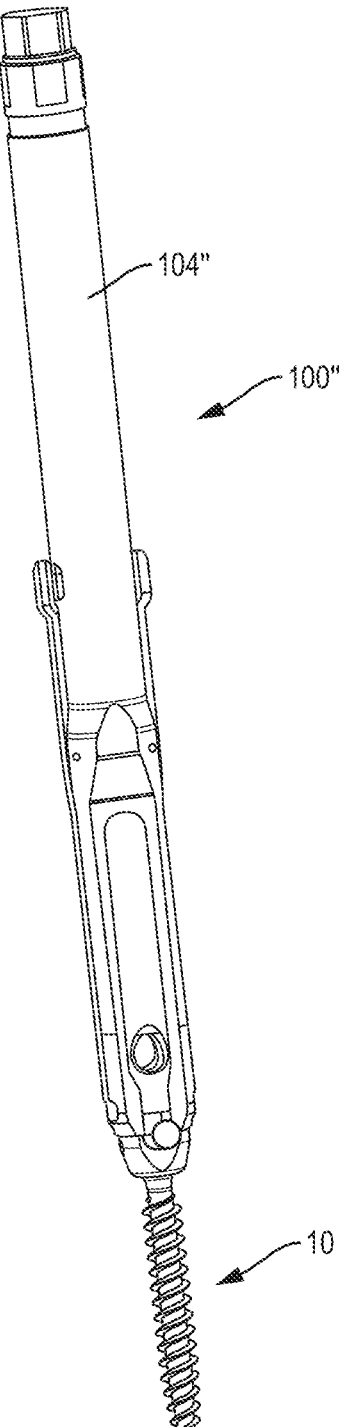
FIG. 7 is a perspective view of another embodiment of a reducer instrument of the present disclosure having an extended inner sleeve.
Figure 8:
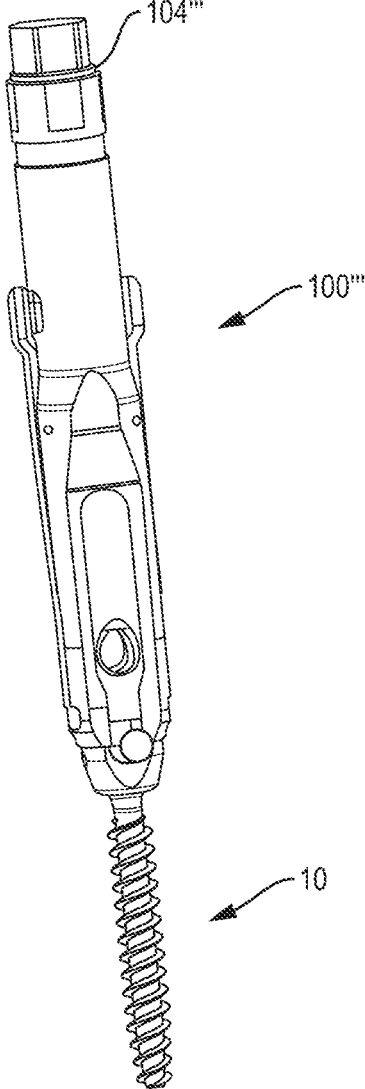
FIG. 8 is perspective view of another embodiment of a reducer instrument of the present disclosure having an intermediate-length inner sleeve.
Figure 47:
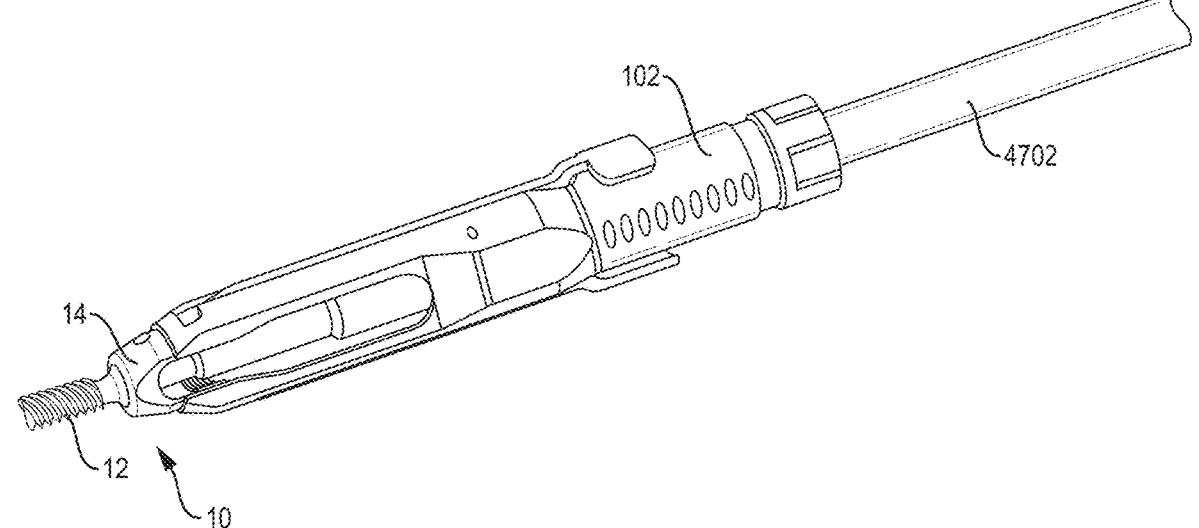
FIG. 47 is a perspective view of one embodiment of a driver instrument extending through an outer sleeve of a reducer instrument that is coupled to a bone anchor to drive an implantable shank of the bone anchor.

In use, the reducer instrument 100 can be positioned such that the pivoting arms 106*a*, 106*b* engage a bone anchor 10 disposed therebetween to dock the reducer instrument 100 to the bone anchor 10, e.g., as shown in FIGS. 6-8. The pivoting arms can be spring-loaded lever arms that are biased to a closed position to enable retention of the screw (or hook) head during rod reduction (FIG. 3 illustrates one example use of coil springs 119 to bias the arms 106*a*, 106*b*). The bone anchor can include a shank 12 and a receiver head or member 14 into which a rod 16 can be reduced. In some embodiments, the reducer instrument can enable insertion of the bone anchor or screw pre-attached to the reducer such that a screw inserter travels through the channel 108 of the outer sleeve 102 to deliver the bone screw into bone, such as a pedicle. As described in more detail below, one example of such a configuration is shown in FIG. 47.

The outer sleeve 102 can include a generally tubular central portion that terminates in first and second extensions 112*a*, 112*b*. The extensions 112*a*, 112*b* have one or more recesses formed therein to receive the extensions 112*a*, 112*b*. The outer sleeve 102 can be defined by a sidewall 114 circumscribing the channel 108. An interior surface of the channel 108 can be threaded or can include other mating features for cooperating with an instrument, such as the inner sleeve 104 inserted therethrough, to advance the instrument longitudinally relative to the outer sleeve 102.

The inner sleeve 104 can include a proximal threaded member 120 and a distal translating member 122. The relationship between the two members is shown in greater detail in FIG. 3. As shown, the threaded member 120 and the translating member 122 can be coupled via a series of radially oriented pins or projections 117 that can protrude from an inner surface of the threaded member 120 and be received within a circumferential groove formed in an outer surface of the distal translating member 122. As shown, a washer 124, e.g., a thrust washer, made of a polymer or gall-resistant metallic material can separate and serve as a bearing surface between the translating and threaded member.

Figure 43:
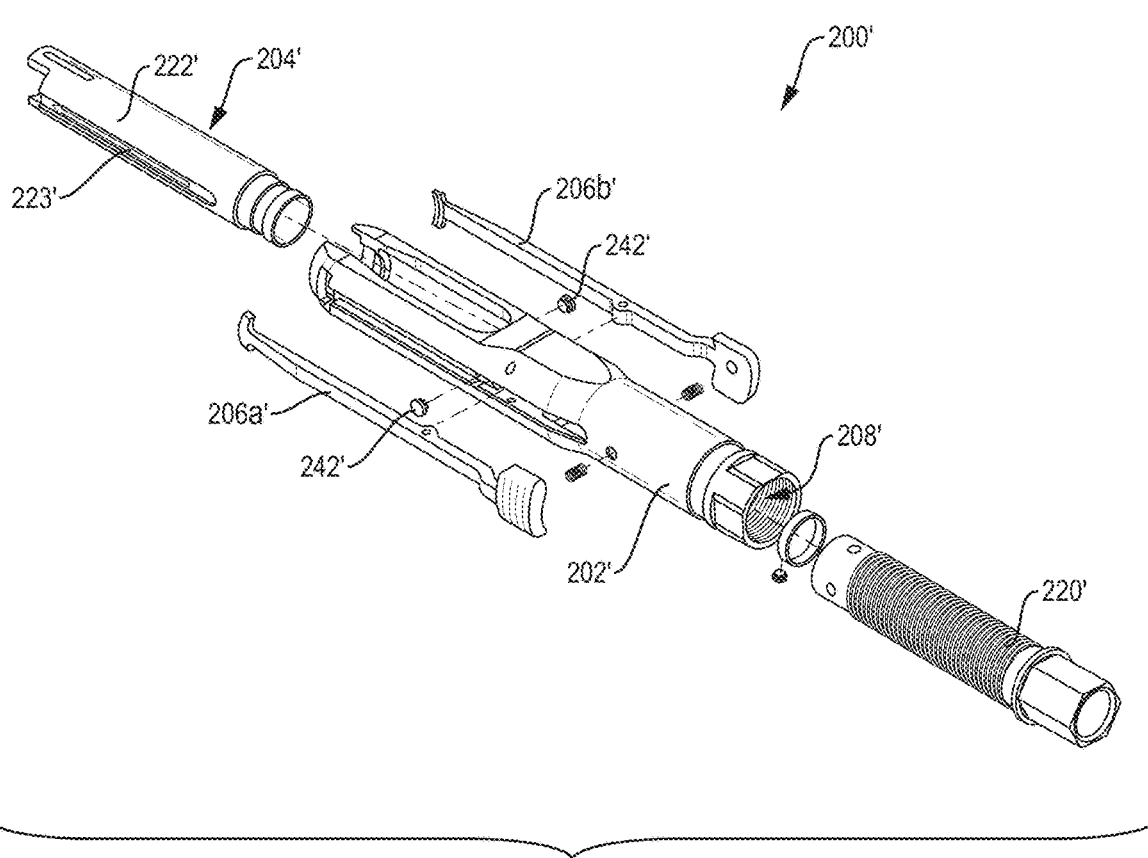
FIG. 43 is an exploded perspective view of one embodiment of a reducer instrument having a pin coupling mechanism.
Figure 44:
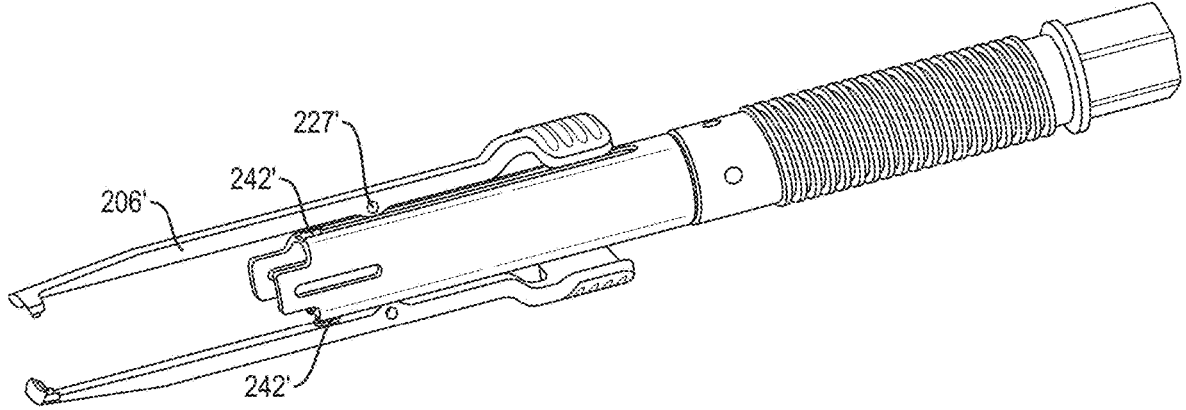
FIG. 44 is a partial perspective view of the reducer instrument of FIG. 43 having the outer sleeve hidden from view.
Figure 45:
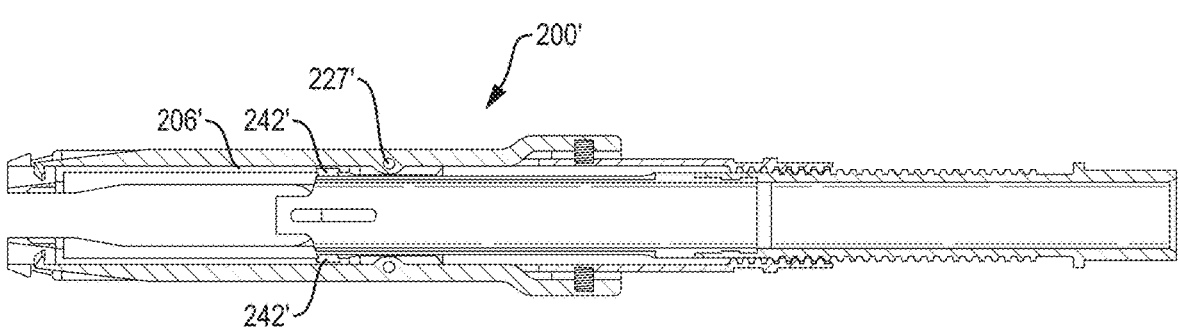
FIG. 45 is a side cross-sectional view of the reducer instrument of FIG. 43.

In some embodiments, the translating member 122 can include one or more longitudinal grooves 123 formed therein. In some embodiments, a nub 127 can be integrally formed on the pivoting arms 106*a*, 106*b* such that no pin is needed to secure it in place. That is, the longitudinal grooves 123 can mate with a cam-like semi-circular surface or nub 127 on the underside of the lever fulcrum to prevent rotation of the translating member during reduction. This can be in lieu of the use of traditional pins to minimize manufacturing, welding, and assembly complexity. In some embodiments, however, one or more pins can be utilized instead of a nub 127, as shown in FIGS. 43-45 and explained in more detail below. Returning to the nub 127, it can extend from a surface of the arm 106 and ride in the longitudinal groove 123 to encourage translation but prevent rotation of the translating member 122.

Figure 4:
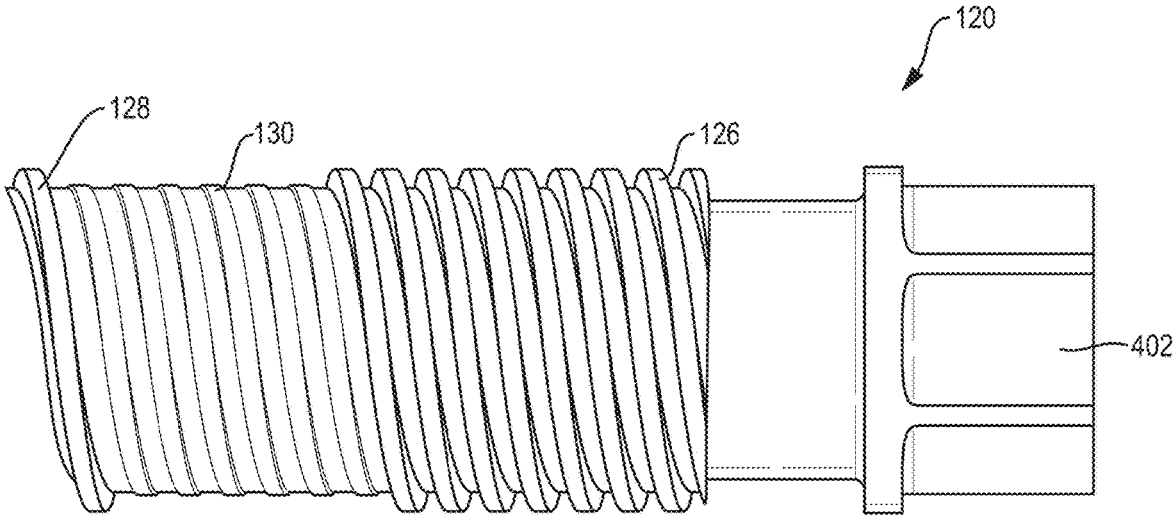
FIG. 4 is a side view of the inner sleeve of the reducer instrument of FIG. 1.

FIG. 4 illustrates the threaded member 120 in greater detail. As shown, the threaded member 120 can include a plurality of threaded portions formed thereon. For example, the threaded member 120 can include a first threaded portion 126 and a second, additional distal threaded portion 128, which can prevent the threaded member 120 from being removed proximally out of the outer sleeve 102 unintentionally, while still enabling complete disassembly from the outer sleeve 102 for cleaning. In use, the first and second threads of the inner sleeve 104 are threaded into the outer sleeve 102 to fully reduce the spinal rod into the bone anchor, while both the first and second threads are to be unwound from the outer sleeve 102 to remove the inner sleeve 104 therefrom. More particularly, the first and second threaded portions can be separated by a non-threaded portion 130. The non-threaded portion 130 can include alternative surface features, such as ribs, nubs, or other features. The presence of the non-threaded portion 130 can allow feedback to a user that they have retracted the inner sleeve 104 subassembly or reducing shaft to a maximum extent, as the inner sleeve 104 will translate freely relative to outer sleeve 102 once the threaded portion 126 is disengaged. To fully disassemble the inner sleeve 104 subassembly from the outer sleeve 102, however, a user will have to both pull proximally to translate the inner sleeve 104 and rotate to engage the second threaded portion 128 at a distal end of the threaded member 120. Only once the second threaded portion 128 is fully disengaged by threading proximally relative to the outer sleeve 102 can the inner sleeve 104 subassembly be completely removed from the outer sleeve. That is, removal of the inner sleeve 104 relative to the outer sleeve 102 is performed with a pull/push force as well as a rotation, which can prevent unwanted backout of the inner sleeve 104.

In some embodiments, the threaded member 120 includes a triple lead stub acme thread to minimize profile, increase speed of reduction, and reduce mechanical advantage to create increased tactile response. Other thread forms are also possible, however. This can be done, for example, to balance performance under various loading conditions (e.g., axial loading vs. side loading, etc.), device size (e.g., required thread outer diameter), etc. For example, in some embodiments a centralizing acme thread can be utilized to provide increased performance under side loading conditions (e.g., greater resistance to thread binding). Still other possible thread forms include trapezoidal, square, and buttress threads. In some embodiments, aspects of one or more thread forms can be combined to create a modified thread form. Further, in some embodiments, the threaded member 120 can include an internal channel defined therein for receiving one or more devices, e.g., a set screw, therethrough.

Figure 46:
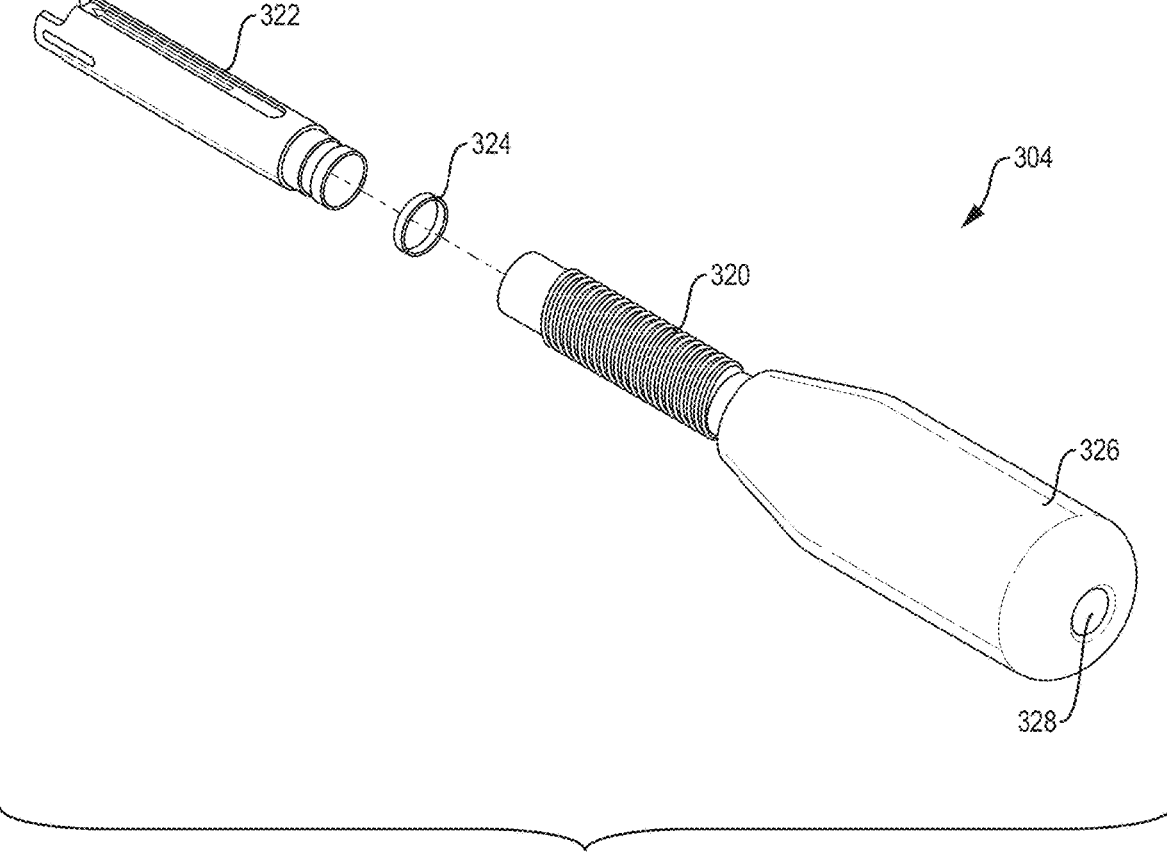
FIG. 46 is an exploded perspective view of another embodiment of the inner sleeve having an integrated proximal handle.

The threaded member 120 can also include a proximal drive interface 402 to facilitate the transmission of torque thereto during use. The proximal drive interface 402 can, in some embodiments, be a modular drive interface including one or more flats or other torque-transmission features formed thereon. In the illustrated embodiment, the proximal drive interface 402 is a hex drive interface comprising of a plurality of flats spaced around the circumference of the member 120. Such a modular drive interface can maintain a low profile/small diameter of the threaded member 120 while facilitating attachment to any of a variety of drivers or other instrumentation when needed. In certain embodiments, any of a variety of user-graspable handles or other structures can be modularly coupled to the threaded member 120 using the proximal drive interface 402. In other embodiments, any of a variety of user-graspable handles or other structures can be integrally formed or otherwise permanently coupled to the threaded member 120 in place of the modular proximal drive feature 402 shown in FIG. 4. FIG. 46 illustrates one embodiment of an inner sleeve 304 having a threaded member 320 integrally formed with a handle 326 at a proximal end thereof.

Figure 5:
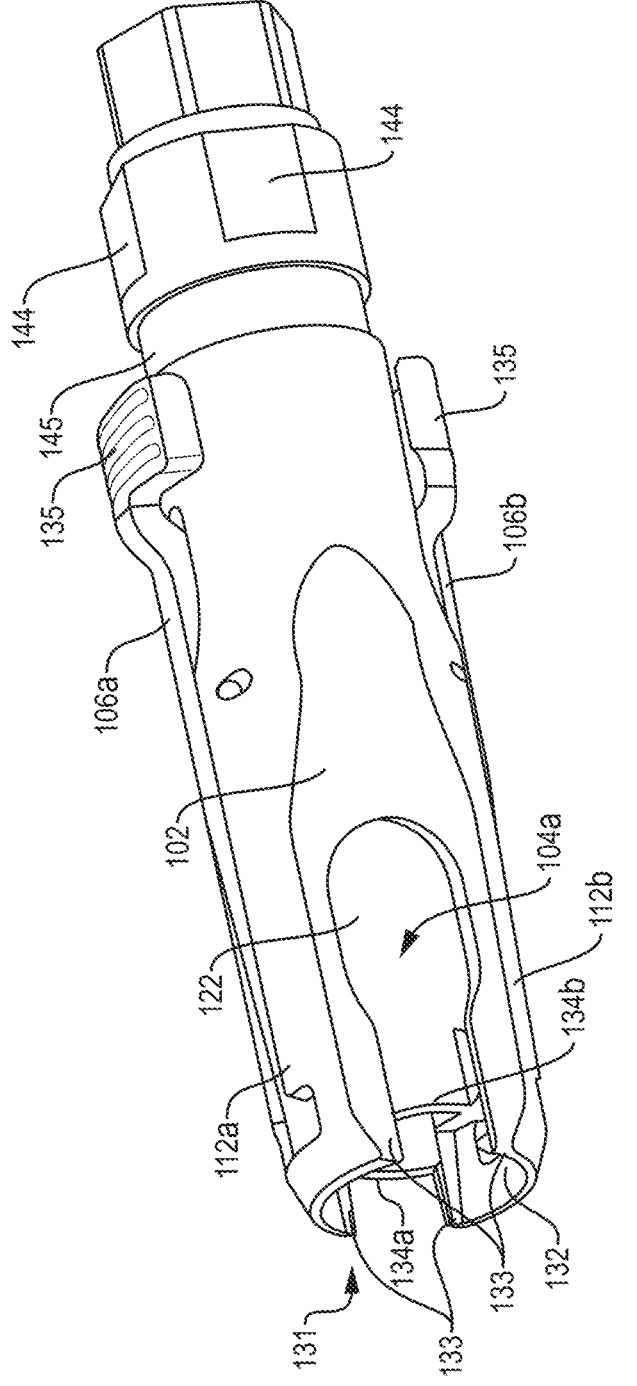
FIG. 5 is a perspective view of another embodiment of a reducer instrument according to the present disclosure.

As shown in FIG. 5, the distal translating member 122 includes first and second static or fixed arms 134a, 134b extending distally therefrom for performing rod reduction. The static arms 134a, 134b can be configured to advance distally without rotating to advance the spinal rod into the receiver member. As shown in FIG. 1, the translating member 122 can include a window 125 therein to enable observation of a set screw when threading into the bone anchor during tightening and loosening, as discussed further below. The window 125 can have a variety of shapes and sizes, including the teardrop shape shown in FIG. 1 or the slit shape shown in FIG. 40. Further, the window 125 can be positioned at a variety of locations along a length of the translating member 122. In some embodiments, the window can be positioned close enough to a distal end of the translating member 122 to permit visualization of a set screw after threading it completely into a receiver member of a bone anchor. In some embodiments, a longer slit shaped window can provide a greater degree of visualization of the set screw during insertion and tightening maneuvers while also maximizing strength and stiffness of the translating member 122 that might be reduced if too much material is removed, especially closer to a distal end of the translating member. Returning to the inner sleeve 104 more generally, it can translate relative to the outer sleeve 102.

FIG. 5 illustrates an embodiment of an inner sleeve 104a without any window disposed within the outer sleeve 102. The outer sleeve 102 has a distal pocket 131 formed between opposed arms 112a, 112b that can accept a receiver member of a bone anchor and couple thereto. The distal pocket 131 can vary in size, though, in some embodiments, the window 131 can be about 9 mm wide. The size and shape of the distal end of the outer sleeve 102 can enable coupling to a bone anchor with some amount of lateral misalignment. Moreover, an internal surface of the arms 112a, 112b can have a shape or profile that is complementary to an outer surface of the bone anchor in order to facilitate coupling even in the event there is some amount of misalignment, whether that be, e.g., lateral or rotational misalignment along an axis of a rod, rotational misalignment along a longitudinal axis of the instrument 100, etc. In some embodiments, for example, an inner surface 132 of each arm 112a, 112b can include a tapered profile complementary to an outer surface of opposed arms of a polyaxial bone anchor receiver head. In some instances, the inner surface 132 of each arm 112a, 112b can include a conical tapering profile that is complementary to the conical tapering profile of a receiver member. Such an arrangement can allow for some pivoting misalignment between the receiver head and the instrument 100 that can be corrected as the instrument is advanced distally relative to the receiver head and the receiver head advanced into the distal pocket 131.

Further, the arms 112a, 112b can include sidewalls 133 extending outward from the inner surface 132 at lateral ends of each arm. The sidewalls 133 can similarly include a tapering profile to aid alignment with a receiver member of a bone anchor, e.g., by self-correcting for rotational misalignment about the longitudinal axis of the instrument as the instrument is advanced distally relative to the bone anchor and the anchor is received within the distal pocket 131. In some embodiments, the opposed, inward-facing surfaces of each sidewall 133 can have a planar tapering profile that can be complementary to a planar tapering profile of abutting surfaces on a bone anchor receiver member. The various tapered surfaces can accommodate misalignment when coupling the instrument 100 to a bone anchor such that advancement of the outer sleeve 102 over the bone anchor 10 forces the two components into proper alignment just prior to positive engagement of the pivoting arms 106a, 106b with the anchor 10 to simplify attachment of the instrument 100 to the anchor 10. As noted, the receiver member 14 can include one or more complementary tapering profiles to the tapered surfaces provided on the outer sleeve. Further details on features of the anchor 10 that can be utilized with the instruments disclosed herein can be found in U.S. Pat. Nos. 10,039,578 and 10,299,839, as well as U.S. Provisional Appl. No. 63/157,362, entitled "Multi-Feature Polyaxial Screw" and filed on Mar. 5, 2021, and U.S. application Ser. No. 17/685,359, entitled "Multi-Feature Polyaxial Screw," filed on Mar. 2, 2022, and claiming priority to the previously-noted provisional application. The entire contents of each of these applications are incorporated by reference herein.

A proximal end of the outer sleeve 102 can include one or more mating features. For example, the outer sleeve 102 can include one or more proximal flats 144 having a square or rectangular shape oriented around a circumference thereof. The flats 144 can be spaced around a circumference of the outer sleeve to couple to a corresponding mating feature of an instrument that engages the outer sleeve. Moreover, the outer sleeve 102 can include a circumferential groove 145 that extends around the circumference of the outer sleeve 102 to facilitate engagement of the outer sleeve to instruments, as discussed further below. As shown, the circumferential groove 145 can be oriented distal to the flats 144, though it will be appreciated that their relative orientation can be reversed.

FIG. 5 also illustrates that, in some embodiments, surgeon-facing actuators can be differentiated from the remainder of the device using different colors, textures, materials, etc. For example, in the embodiment of FIG. 5 the surgeon-manipulated actuators 135 of the arms 106a, 106b can be colored black using, e.g., aluminum-titanium-nitride (AI-TiN) coating, etc.

A length of the inner sleeve can vary. FIG. 6 illustrates a reducer instrument 100' having a shorter inner sleeve 104'. The inner sleeve 104' can provide approximately 20 mm of axial rod reduction in some embodiments. Use of the short inner sleeve 104' can prevent proximal crowding at lordotic/concave segments, or be especially useful in pediatric applications where space is limited.

FIG. 7 illustrates a reducer instrument 100'' having a longer inner sleeve 104''. The inner sleeve 104'' can provide approximately 60 mm of axial rod reduction in some embodiments. In some embodiments, the extended length can be achieved by welding or otherwise coupling two or more components to create the inner sleeve. When using the extended length sleeve 104'' with an increased range of reduction, an alternate surgical technique can be possible where the rod is inserted after coupling a reducer to an anchor.

FIG. 8 illustrates a reducer instrument 100'' having an inner sleeve 104'' of intermediate length between those shown in FIGS. 6 and 7. This medium length inner sleeve 104''' can provide approximately 40 mm of axial rod reduction in some embodiments and can be suitable to many applications.

Figures 9D, 9E, 9F:
FIG. 9D is a side cross-sectional view of the reducer instrument of FIG. 7 engaging a bone anchor with the inner sleeve disposed at a distal position.
FIG. 9E is a side cross-sectional view of the reducer instrument of FIG. 8 engaging a bone anchor with the inner sleeve disposed at a distal position.
FIG. 9F is a side cross-sectional view of the reducer instrument of FIG. 6 engaging a bone anchor with the inner sleeve disposed at a distal position.

FIGS. 9A-9F illustrate cross-sectional views of the reducer instrument 100 having various length inner sleeves 104 disposed therein. More particularly, each of the figures illustrates reducer instruments 100 having varying lengths of the inner sleeve engaging bone anchors with their respective pivoting arms 106a, 106b. FIGS. 9A and 9D, for example, illustrate the range of axial reduction possible for the instrument 100'' shown in FIG. 7, as FIG. 9A shows the instrument 100'' with the inner sleeve 104'' in a proximal position and FIG. 9B shows the instrument 100'' with the inner sleeve 104'' in a distal position. This pattern is repeated in FIGS. 9B and 9E with regard to the intermediate-length instrument 100''' of FIG. 8, and in FIGS. 9C and 9F with regard to the shorter instrument 100' of FIG. 6.

Figure 10:
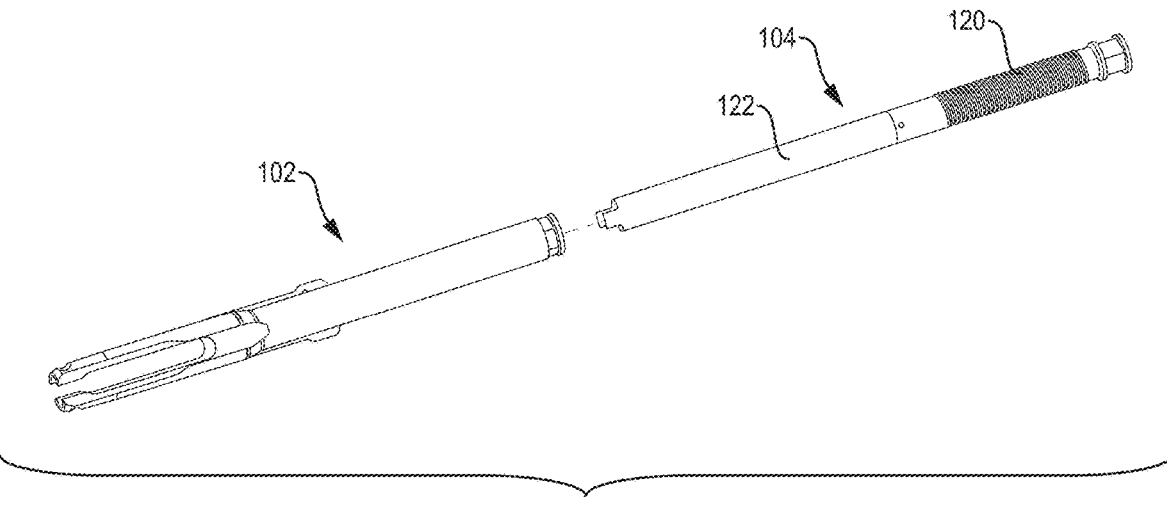
FIG. 10 is an exploded perspective view of one embodiment of a reducer instrument of the present disclosure.
Figure 11:
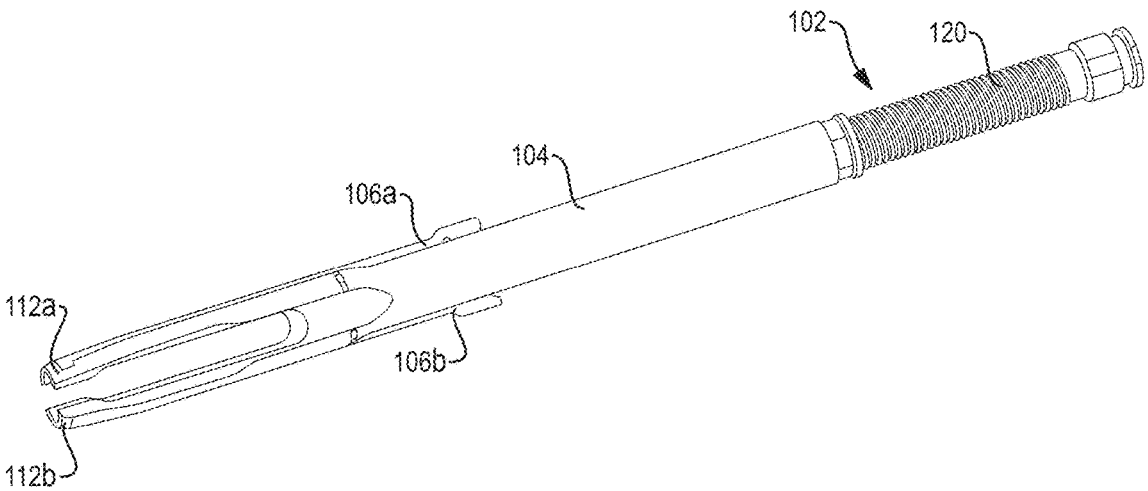
FIG. 11 is a perspective view of the instrument of FIG. 10.

FIG. 10 illustrates one embodiment of an assembly of a reducer instrument 100 of the present disclosure and FIGS. 10-23 illustrate one embodiment of a method for utilizing such an instrument. Referring to instrument 100 shown in FIG. 10, the inner sleeve 104 can translate distally through an opening in the outer sleeve 102 to dispose the translating member 122 therein. Once assembled, as shown in FIG. 11, the threaded member 120 can extend proximally from the outer sleeve 104 while the translating member 122 remains disposed therein for distal advancement towards the extensions 112a, 112b of the outer sleeve as the threaded member 120 is rotated relative to the outer sleeve 102.

Figure 12:
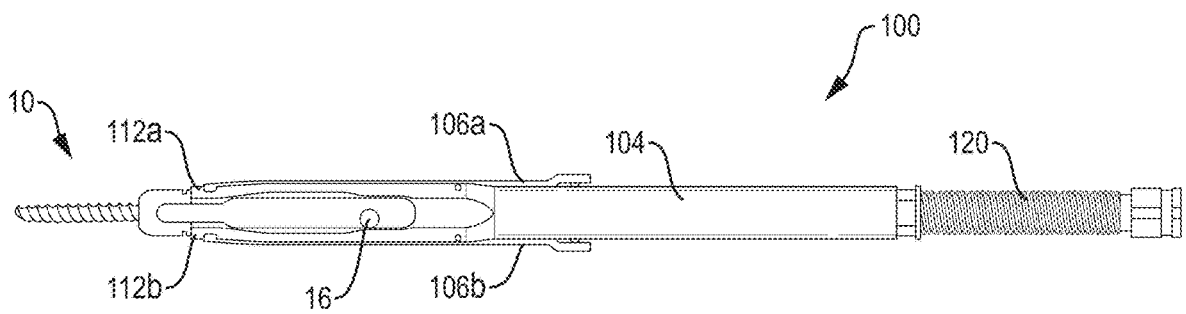
FIG. 12 is a side view of the reducer instrument of FIG. 10 disposed over a spinal rod and adjacent to a bone anchor.

FIG. 12 illustrates the reducer instrument 100 engaged over a rod 16 and adjacent to a bone anchor or pedicle screw 14. As shown, the spinal rod 16 can be disposed between the pivoting arms 106a, 106b and extensions 112a, 112b of the outer sleeve 102 while the receiver member 14 is disposed distal to the outer sleeve 102. The outer sleeve 102 can be advanced towards the bone anchor 10 to engage a notch thereof. FIG. 12 illustrates an embodiment wherein the reducer instrument 100 is advanced distally to first pass over and capture the rod 16 between the extensions 112a, 112b, followed by an approach the bone anchor 14. In other embodiments, however, the reducer instrument can be coupled to the bone anchor prior to rod placement. In such embodiments, the rod can be introduced into the space between the extensions 112a, 112b laterally. Further discussion regarding such embodiments is below.

Figure 13:
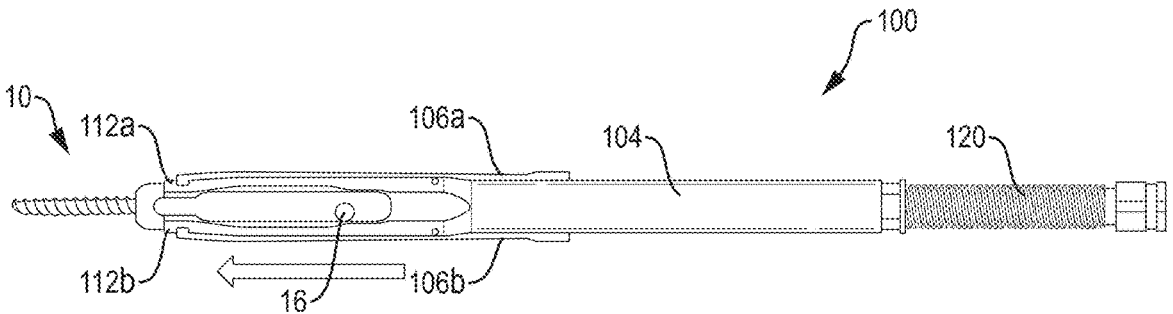
FIG. 13 is a side view of the reducer instrument of FIG. 12 coupling to the bone anchor.

FIG. 13 illustrates the reducer instrument 100 engaging the receiver member 14. As shown, during engagement, the pivoting arms 106a, 106b move radially outward at their distal ends to go over the notch of the receiver member while the outer sleeve 102 is disposed over the receiver member. Once the outer sleeve 102 has sufficiently advanced over the receiver member 14, the distal ends of the pivoting arms 106a, 106b move back radially inwards toward the receiver member to click into place (e.g., as a result of a biasing force, such as a radially outward spring force exerted on a proximal end of the pivoting arms). As mentioned above, the tapered sidewalls 132 allow for some amount of initial rotational misalignment between the outer sleeve 102 and implant head 14 during engagement along the axis of the device 100.

Figure 14:
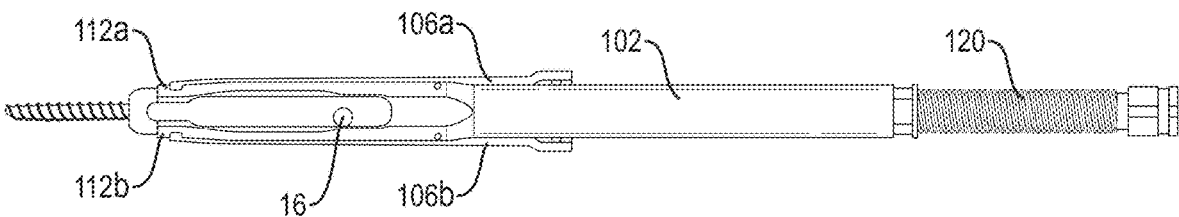
FIG. 14 is a side view of the reducer instrument of FIG. 12 docked to the bone anchor.

FIG. 14 illustrates the reducer instrument 100 docked to the pedicle screw 10 with the rod 16 disposed between the pivoting arms 106a, 106b and extensions 112a, 112b of the outer sleeve 102. The above-described process for assembling the reducer instrument 100 and/or coupling the outer sleeve 102 of the reducer instrument to a bone anchor can be performed in a variety of orders, allowing flexibility for different surgical workflows that can enhance efficiency and accommodate different user preferences. For example, assembly of the inner and outer sleeve components of the instrument 100 can be performed at a "back table" or surgical prep area before passing the assembled instrument to a surgeon for use. In addition, a bone anchor can be coupled to the outer sleeve 102 before or after implantation in a patient and/or before or after assembly of the outer sleeve 102 and the inner sleeve 104.

In certain embodiments, for example, the outer sleeve 102 can be coupled to a bone anchor prior to implanting the bone anchor into a patient and the bone anchor can be implanted using an instrument that passes through the outer sleeve 102 to couple with the implantable shank of the bone anchor. This can be done with or without the inner sleeve 104 being coupled to the outer sleeve 102. In embodiments where a bone anchor is implanted with the outer sleeve 102 coupled thereto and without the inner sleeve 104, the inner sleeve can be coupled to the outer sleeve 102 after the bone anchor is implanted and the driver instrument is removed from the outer sleeve 102.

FIG. 47 illustrates one embodiment of a driver instrument 4702 extending through an outer sleeve 102 of a reducer instrument that is coupled to a receiver member 14 of a bone anchor 10. The driver instrument 4702 is shown coupled to an implantable shank 12 of the bone anchor 10 such that rotation of the driver instrument can cause rotation of the implantable shank to drive it into bone. As noted above, once the implantable shank 12 is disposed in bone, the driver instrument 4702 can be removed proximally to separate from the shank 12 and withdraw from the lumen of the outer sleeve 102. An inner sleeve 104 can then be coupled to the outer sleeve 102 to continue the process of rod capture and reduction disclosed herein (e.g., a rod can be introduced laterally through a rod slot of the outer sleeve and the inner sleeve can be rotated relative to the outer sleeve to effect axial reduction of the rod toward the bone anchor 10).

This flexibility of assembly can permit, for example, a workflow in which the reducer instrument 100 is coupled to a bone anchor and a driver instrument at a "back table" or surgical prep area. The assembly can then be passed to a surgeon or other user ready for use to implant the bone anchor in the patient. Following implantation, the driver instrument can be removed, leaving the reducer instrument 100 coupled to the implanted bone anchor and ready for use in reducing a rod as described below. In embodiments where the outer sleeve 102 is coupled to a bone anchor prior to implantation or otherwise prior to rod placement generally proximate to the bone anchor, the rod can later be placed by passing it laterally through the rod slot opening of the outer sleeve 102 between the extensions 112a, 112b.

Figure 15:
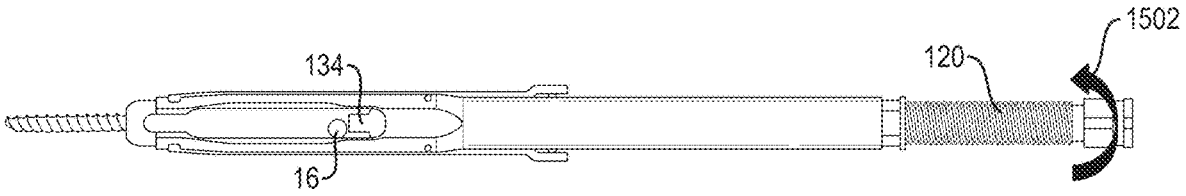
FIG. 15 is a side view of initial rod reduction with the reducer instrument of FIG. 12.

FIG. 15 illustrates a rotation force 1502 being applied to the threaded member 120 to advance the translating member 122 towards the spinal rod. As shown, the threaded member 120 can rotate while the translating member 122 advances in a distal motion to allow the static arms 134 to engage the spinal rod 16.

Figure 16:
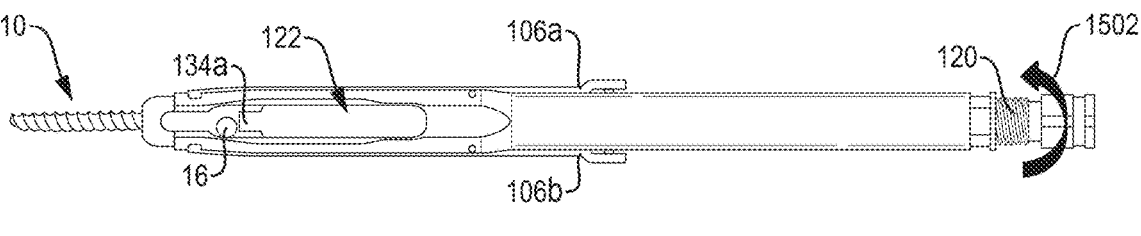
FIG. 16 is a side view of intermediate rod reduction with the reducer instrument of FIG. 12.

FIG. 16 shows further rotation of the threaded member 120 in which the static arms 134a, 134b advance the spinal rod 16 towards the bone anchor 10.

Figure 17:
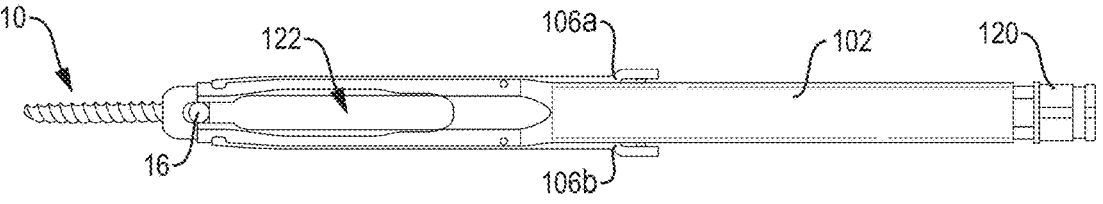
FIG. 17 is a side view of distal rod reduction with the reducer instrument of FIG. 12.

FIG. 17 shows the threaded member 120 abutting the outer sleeve 104 such that the threaded member 120 is at a distal-most position and cannot proceed distally. In this orientation, the spinal rod 16 is reduced within the bone anchor 10.

Figure 21:
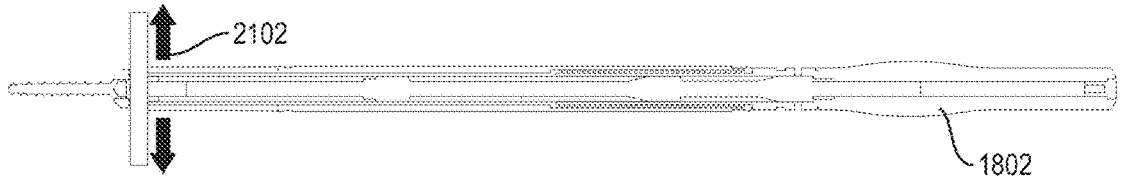
FIG. 21 is a side cross-sectional view of a distraction maneuver performed on the reducer instrument of FIG. 12.

FIGS. 18 and 19 illustrate a set screw 140 being inserted through a channel 142 in the inner sleeve 104 and threaded into the bone anchor receiver member using an inserter 1802. In some embodiments, the inserter can be used to provisionally tighten the set screw to the bone anchor, as shown in FIG. 19 by the application of a rotational force 1902. The set screw 140 can be advanced distally through the inner sleeve 104, e.g., through the threaded member 120 and the translating member 122, to engage the spinal rod to lock the spinal rod to the bone anchor. Further, a derotation maneuver can be performed, as shown in FIG. 20 by arrow 2002, or a distraction maneuver can be performed, as shown in FIG. 21 by arrow 2102, using the inserter when disposed through the inner sleeve 104 to introduce and drive the set screw 140. In other embodiments, such derotation and/or distraction maneuvers can be performed using the instrument 100 without any inserter present.

Figure 22:
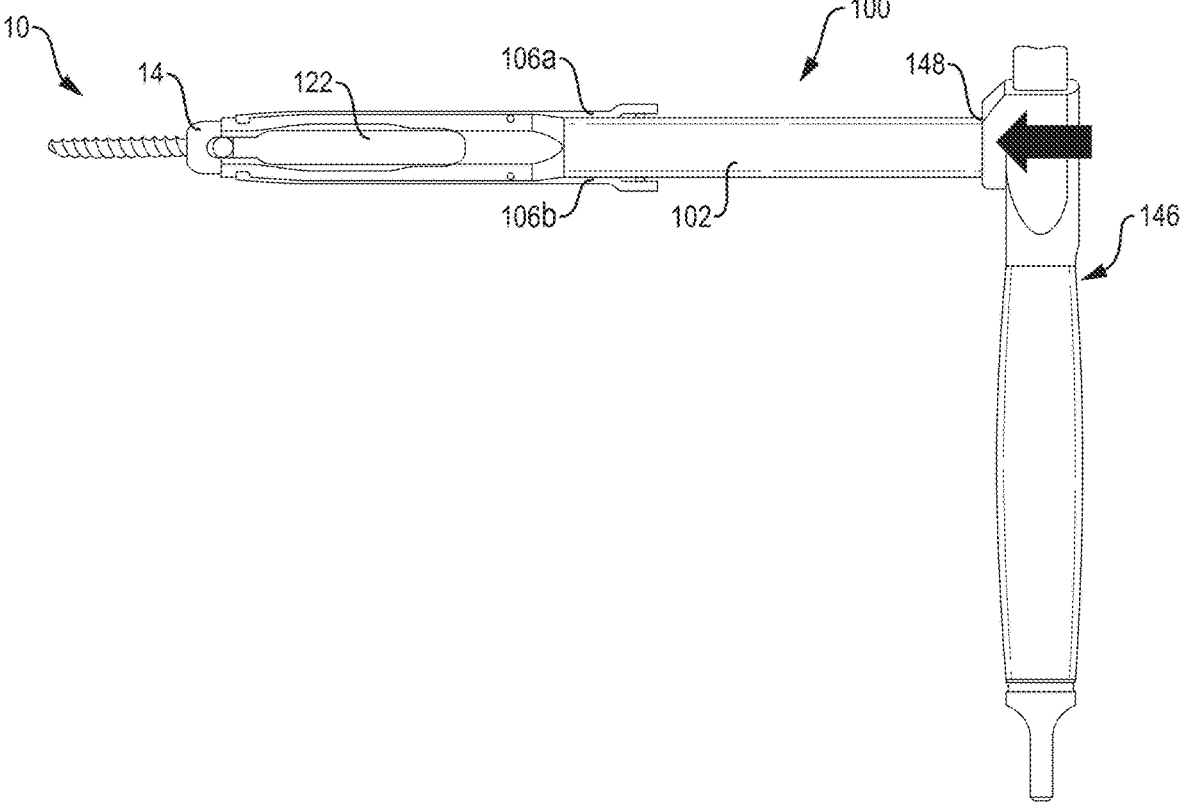
FIG. 22 is a side view of a counter-torque device coupled to the reducer instrument of FIG. 12.
Figure 23:
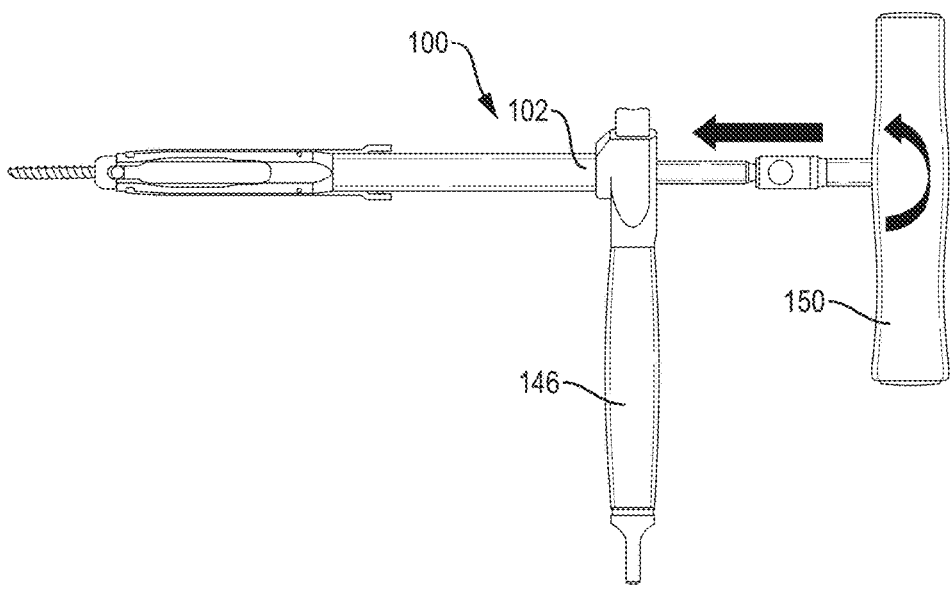
FIG. 23 is a side view of a driver introduced into the inner sleeve of the reducer instrument of FIG. 22.

Final tightening of the set screw 140 can require the application of counter-torque given the forces involved. FIG. 22 illustrates a counter-torque device 146 disposed on the outer sleeve 102. The counter-torque device 146 can couple to the proximal flats 144 and the groove 145 on the outer sleeve 102 to form a positive connection therewith that prevents relative rotation between the components. The proximal flats 144 can be spaced in a manner that allows a corresponding mating feature 148 of the counter-torque device 146 to couple in multiple orientations (e.g., the flats can be formed in a hex or other pattern around a circumference of the instrument to allow coupling at a variety of rotational orientations relative to the instrument). As shown in FIG. 23, a driver 150 can be introduced through the inner sleeve 104 to engage the set screw and perform tightening with the aid of the counter-torque device 146 that locks the rod within the receiver member of the anchor.

Figure 24:
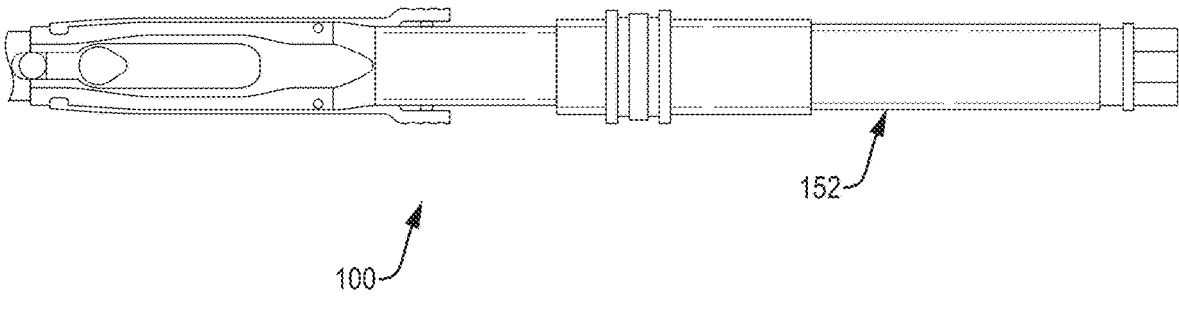
FIG. 24 is a side view of a modular derotation sleeve coupled to the outer sleeve of the reducer instrument of FIG. 1.

In addition, a modular derotation sleeve or tube 152 can also be utilized to couple with the outer sleeve 102 of the instrument 100 and bypass the threaded inner sleeve. Directly engaging the flats of the outer sleeve 102 can allow the application of counter-torque directly through the derotation sleeve 152 via connection to the same type of modular counter-torque device 146 shown in FIGS. 22 and 23. This is in contrast to other devices that provide coupling through an inner threaded sleeve component. FIG. 24 illustrates a modular derotation sleeve 152 coupled to an instrument 100.

Figure 25:
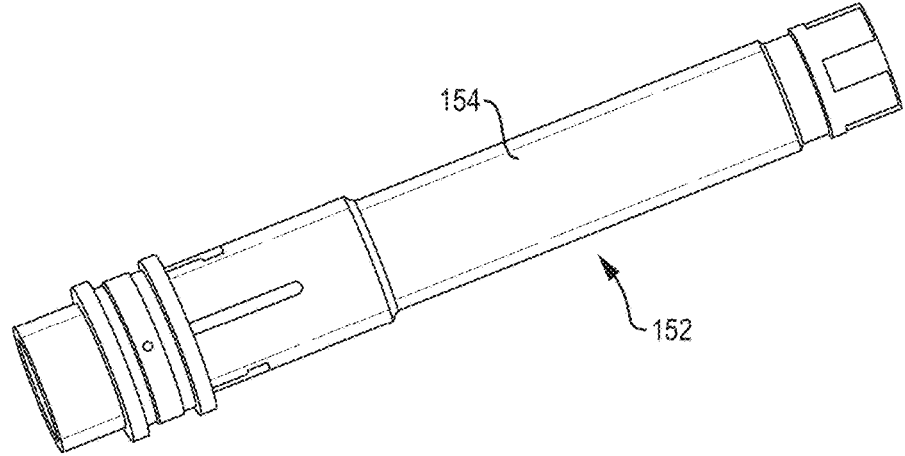
FIG. 25 is a perspective view of the modular derotation sleeve of FIG. 24.
Figure 26:
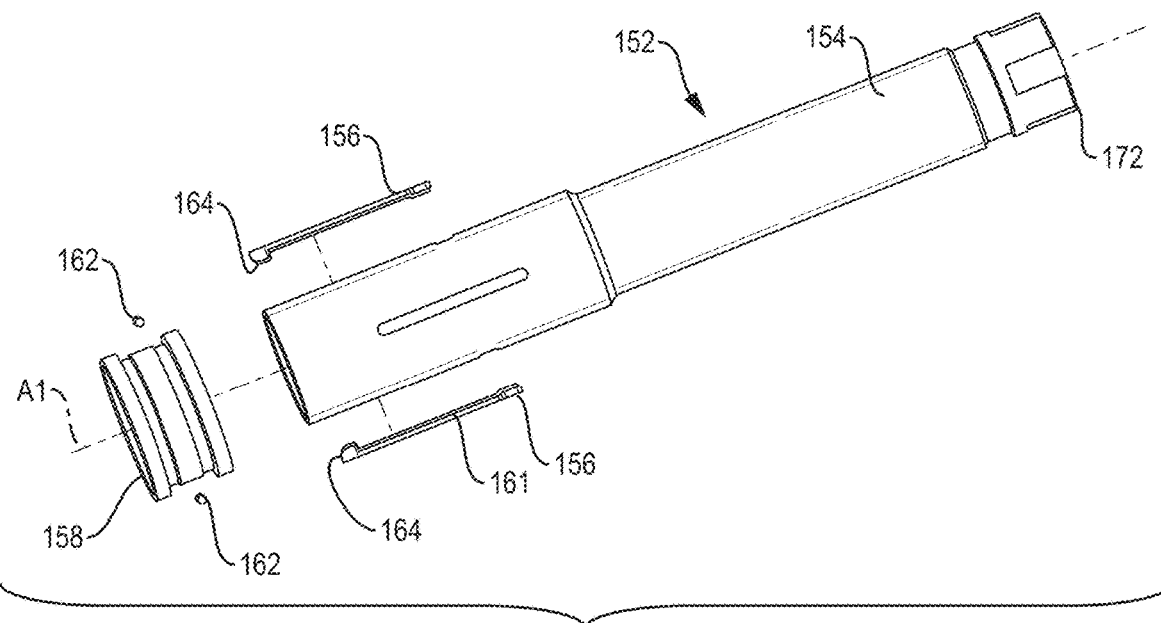
FIG. 26 is an exploded perspective view of the modular derotation sleeve of FIG. 24.
Figure 27:
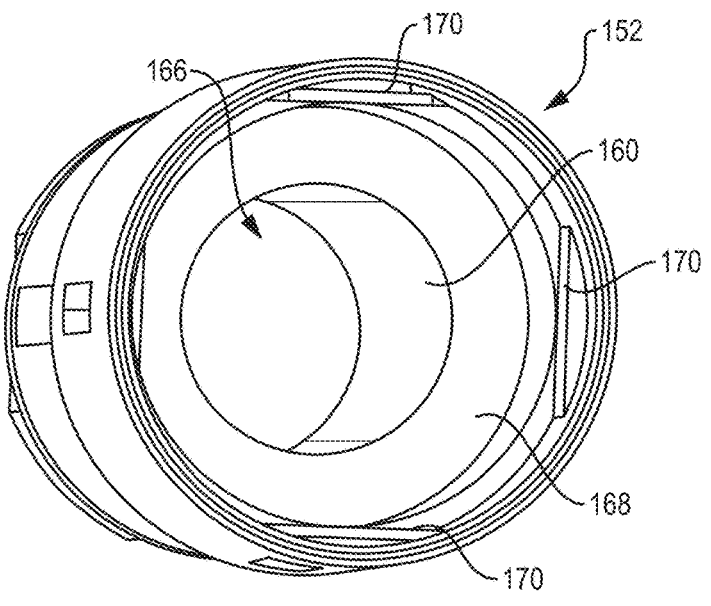
FIG. 27 is a detail perspective view of a distal end of the modular derotation sleeve of FIG. 24.

FIGS. 25-27 illustrate a derotation sleeve 152 that can be coupled to the outer sleeve 102 in greater detail. The derotation sleeve 152 can be used to provide additional leverage when manipulating a vertebra or other bone to which the sleeve is coupled. For example, the derotation sleeve 152 can facilitate application of derotation, distraction, compression, or other forces to a vertebra or to a fixation construct, e.g., to correct a spinal angle, deformity, or other condition of the patient. The derotation sleeve can also provide an attachment point for a derotation rack, navigation system, or other surgical instrumentation.

The derotation sleeve 152 can include a tubular shaft 154 having one or more hinged arms or leaf springs 156 for engaging with the reducer device 100 or other instrument to secure the derotation sleeve 152 thereto. The derotation sleeve 152 can include a locking ring 158 for selectively maintaining the arms 156 in engagement with the reducer instrument 100 or another instrument. The sleeve 152 can include an interior sidewall that defines a lumen or working channel 160 that extends through the shaft. The locking ring 158 can be disposed around an outer surface of the sleeve 152 to move axially relative thereto. The locking ring 158 can be coupled to the sleeve 152 via one or more pins 162 inserted therethrough.

The hinged arms 156 can be configured to grasp a drive interface of an instrument inserted therethrough. The hinged arms 156 can be movable between an open configuration in which an instrument can be inserted and removed from the derotation sleeve 152 and a closed position in which an instrument is captured or retained within the derotation sleeve. The locking ring 158 can be disposed in an unlocked position in which the hinged arms 156 are free to move, or pivot, relative to the derotation sleeve 154, and a locked position in which the hinged arms 156 are constrained from moving relative to the sleeve 154. The hinged arms 156 can pivot radially-inward and/or radially-outward relative to a longitudinal axis A1.

The hinged arms 156 can include a body 161 having a protrusion 164 at a distal end thereof. The body 161 can be pivoted radially inward to bring the protrusion 164 into the lumen 160 to grasp an instrument or other object inserted therethrough. The locking ring 158 can axially slide over the hinged arms 156 to move the arms from the open configuration to the closed configuration and/or to prevent the arms 156 from moving relative to the sleeve 152, thereby locking the arms in the closed configuration.

The derotation sleeve 152 can include a distal drive interface 166 configured to mate with the proximal flats on the outer sleeve 102. The drive interface 166 can be in communication with the lumen 503 such that tools inserted through the drive interface 166 can pass through at least a portion of the lumen 160, and tools inserted through the lumen 160 can pass through at least a portion of the drive interface 166. The drive interface 166 and the lumen 160 can be separated by an abutment surface or shoulder 168 that is defined by an interior sidewall of the derotation sleeve 152, to prevent an instrument inserted into the drive interface 166 from advancing too far proximally into the lumen 160.

A proximal end of the derotation sleeve 152 can include flats 172 that resemble those formed on the outer sleeve 102, thereby enabling connection of the same modular handle to both subassemblies, and therefore the application of countertorque to both subassemblies via the same handle. In some embodiments, a length of the proximal end portion of the derotation sleeve 152 including the flats 172 can be extended to provide a larger surface area for engagement by various instruments that couple thereto.

Figure 28:
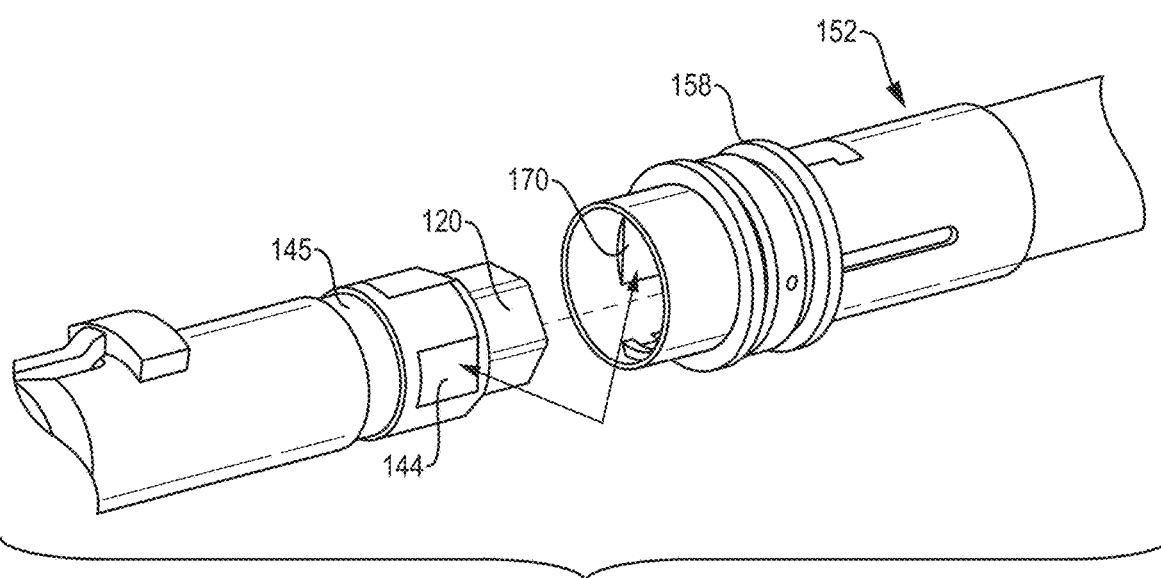
FIG. 28 is a perspective view of the modular derotation sleeve of FIG. 24 coupling to the outer sleeve of the reducer instrument of FIG. 1.

FIG. 28 illustrates the derotation sleeve 152 coupling to the outer sleeve 102 while bypassing the threaded member of the inner sleeve. For example, the derotation sleeve 502 can include one or more engagement surfaces 170 positioned in the drive interface 166 or lumen 160. As shown, the engagement surfaces 170 can protrude at various angles from an interior surface of the derotation sleeve 152 to engage the proximal flats 144 formed on the outer sleeve 102. In this manner, the derotation sleeve 152 makes a positive connection with the outer sleeve 102 while the threaded member 120 of the inner sleeve 104 remains disposed in the channel of the derotation sleeve 152 without engagement from the derotation sleeve 152. As a result, the derotation sleeve 152 can remain fixed relative to the outer sleeve 102 to be capable of exerting derotating forces on the vertebra without rotating relative thereto. As shown in FIG. 27, the abutment surfaces 170 can be positioned at roughly 90-degree angles relative to one another to abut the flats to facilitate coupling and restrict rotation of the derotation sleeve 152 relative to the outer sleeve 102. In other embodiments, however, fewer or additional abutment surfaces 170 can be employed and spaced around a circumference of the sleeve 152, with corresponding flats 144 disposed around a circumference of the outer sleeve.

Figure 29:
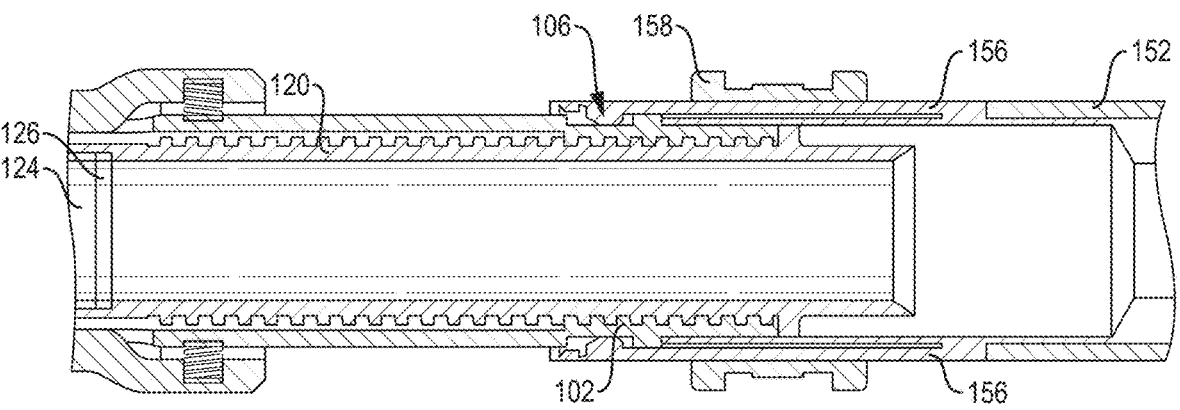
FIG. 29 is a side cross-sectional view of a coupling between the modular derotation sleeve of FIG. 24 and the outer sleeve of FIG. 1.
Figure 30:
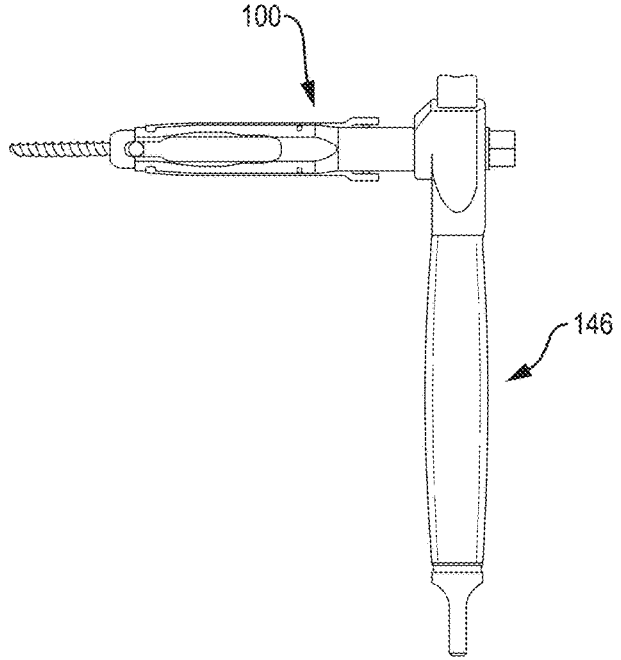
FIG. 30 is a side view of the counter-torque device of FIG. 22 coupled to the reducer instrument of FIG. 1.
Figure 31:
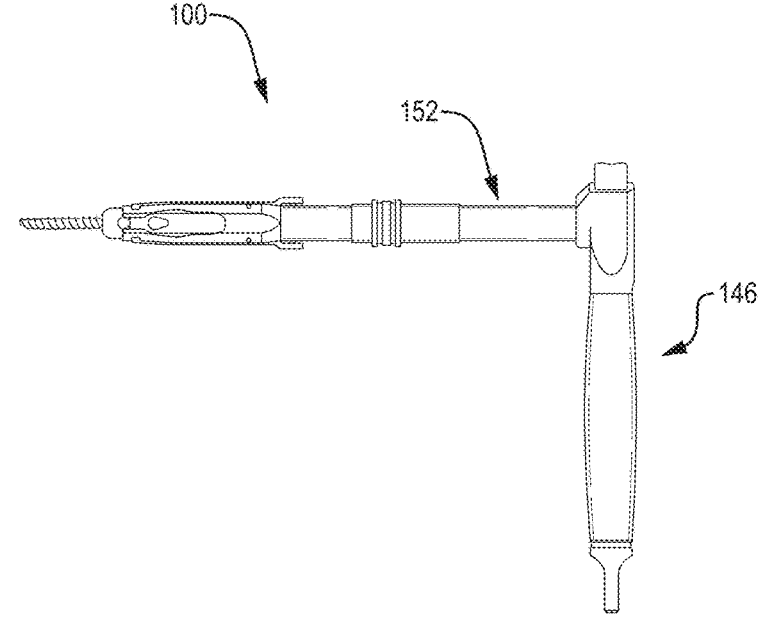
FIG. 31 is a side view of the counter-torque device of FIG. 22 coupled to the assembly of FIG. 24.

FIG. 29 illustrates a cross-sectional view of a coupling between the outer sleeve 102 and the derotation sleeve 152. As discussed above, retention of the derotation sleeve 152 can be achieved via the locking ring 158 that constrains the hinged arms 156 that engage the circumferential groove 145 on the outer sleeve. As noted above, the proximal end of the derotation sleeve 152 can include flats 172 that resemble those formed on the outer sleeve, thereby enabling connection of the same modular handle to both subassemblies, and therefore the application of countertorque to both subassemblies via the same handle. This can be seen, for example, in FIG. 30 where a modular counter-torque instrument 146 like that shown in FIGS. 22 and 23 is shown coupled to an instrument 100 directly, as well as FIG. 31 where the counter-torque instrument 146 is shown coupled to a modular derotation sleeve 152 that is, in turn, coupled to the instrument 100.

Figure 32:
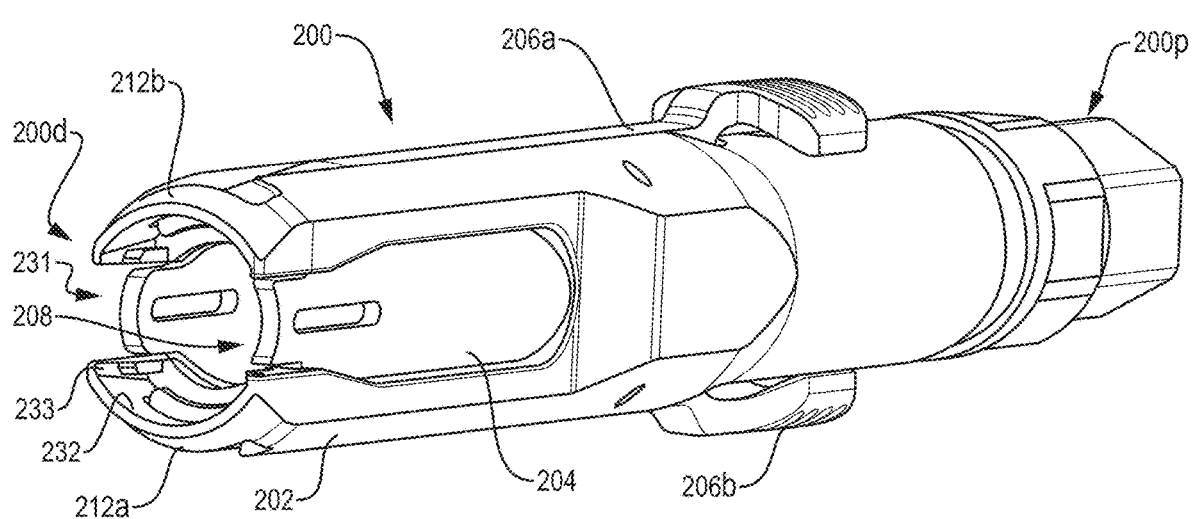
FIG. 32 is a perspective view of one embodiment of a reducer instrument of the present disclosure.
Figure 33:
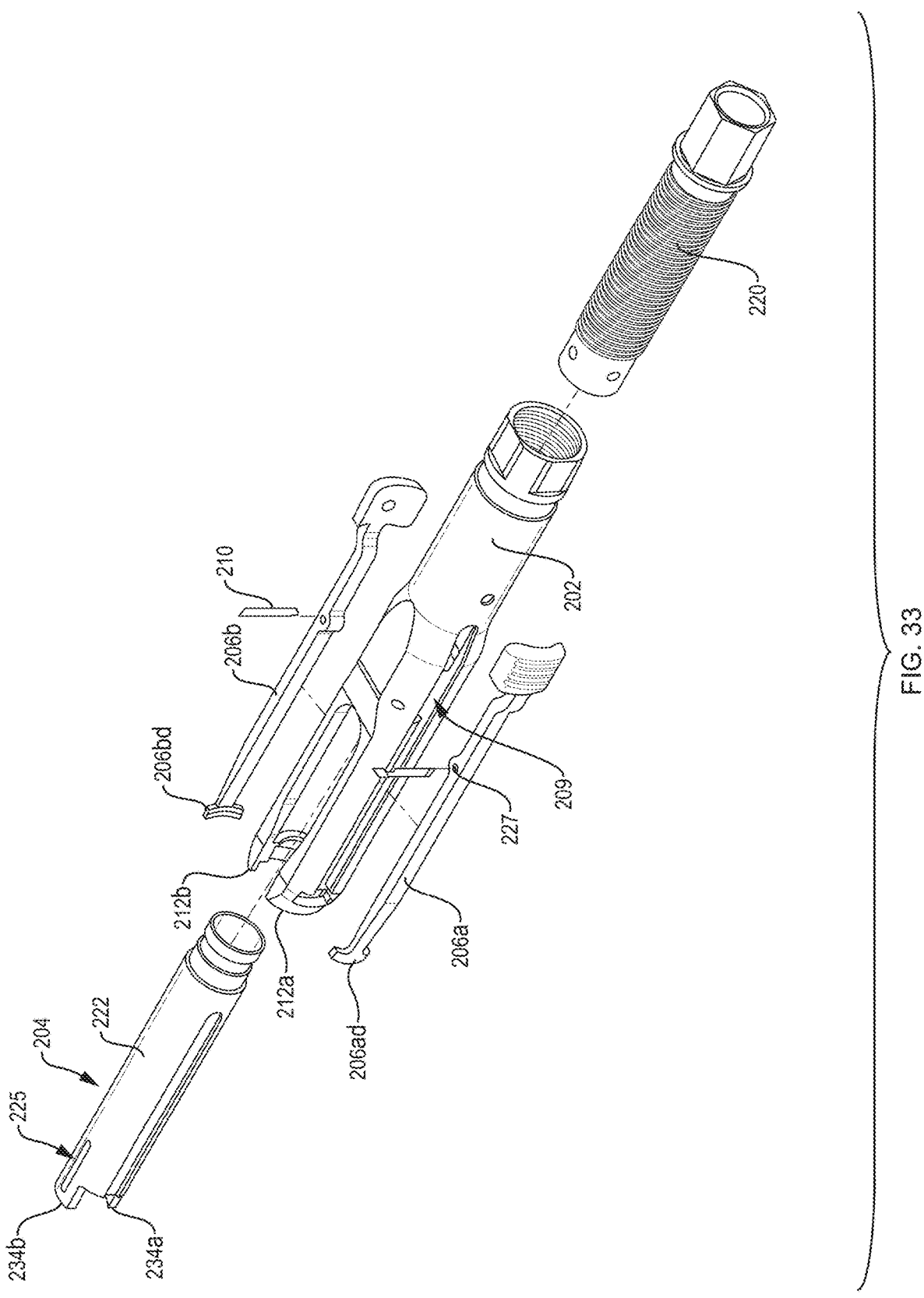
FIG. 33 is an exploded perspective view of the reducer instrument of FIG. 32.

FIGS. 32 and 33 illustrate another embodiment of a reducer instrument 200 of the present disclosure. The reducer instrument 200 can be similar in many respects to the instruments described above and, as a result, a detailed description of every feature is omitted for the sake of brevity.

As shown, the reducer instrument 200 can include an outer sleeve 202, an inner sleeve 204, and a pair of pivoting arms 206 attached to the outer sleeve 202. As with the embodiment discussed in FIG. 1, the outer sleeve 202 can define a working channel 208 configured to receive at least a portion of another tool or instrument, e.g., the inner sleeve 204. The channel 208 can provide access to a surgical site to allow passage of instruments or implants therethrough. The channel 208 can extend from a proximal end 200p of the reducer instrument 200 to a distal end 200d of the reducer instrument. The pivoting arms 206 can be disposed within opposing recesses 209 formed in the outer sleeve 202. The distal ends 206ad, 206bd of the pivoting arms 206a, 206b and nubs 227 of the pivoting arms 206a, 206b can pass into the channel 208, as described further below. Inclusion of the recesses 209 can dispose the pivoting arms 206a, 206b closer to the body of the reducer instrument 200 to narrow the overall profile of the instrument to prevent the arms from interfering with body tissues, other surgical equipment, and the like. Pins 210 can couple the arms 206 to the outer sleeve 202. In use, the reducer instrument 200 can be positioned such that the pivoting arms 206a, 206b engage the bone anchor 10 disposed therebetween to dock the reducer instrument 200 to the bone anchor 10, e.g., as shown in FIG. 34, and discussed in greater detail below.

Each pair of static or fixed arms 234a, 234b for performing rod reduction can include a window 225 formed therein to enable observation of a set screw when threading into the bone anchor during tightening and loosening. As shown, the window 225 can be shaped as a narrow slit that extends along a length of the static arms 234a, 234b to allow for visibility of the set screw, or another instrument, as it travels through the reducer instrument 200 for engaging the bone anchor. The window 225 can extend farther distally compared to the window 125 in FIG. 1 to enable better visualization of the set screw once the set screw has been tightened into the bone anchor. In some embodiments, the size of the window 225 can vary based on a size of the inner sleeve 204, e.g., its diameter, length, thickness, etc. For example, as discussed above with respect to FIGS. 6-8, a size of the inner sleeve 204 can vary, with each inner sleeve size having a corresponding window size, though in some embodiments different size windows can be formed on different size inner sleeves in various combinations to provide maximum set screw visibility.

The outer sleeve 202 can include a generally tubular central portion that terminates in first and second extensions or arms 212a, 212b. The extensions 212a, 212b can include sidewalls 233 extending from an inner surface 232 at the lateral ends of each arm 212a, 212b. The sidewalls 233 can include a tapering profile to aid alignment with a receiver member of a bone anchor. The outer sleeve 202 has a distal pocket 231 formed between opposed arms 212a, 212b that can accept a receiver member of a bone anchor 10 and couple thereto.

Figure 34:
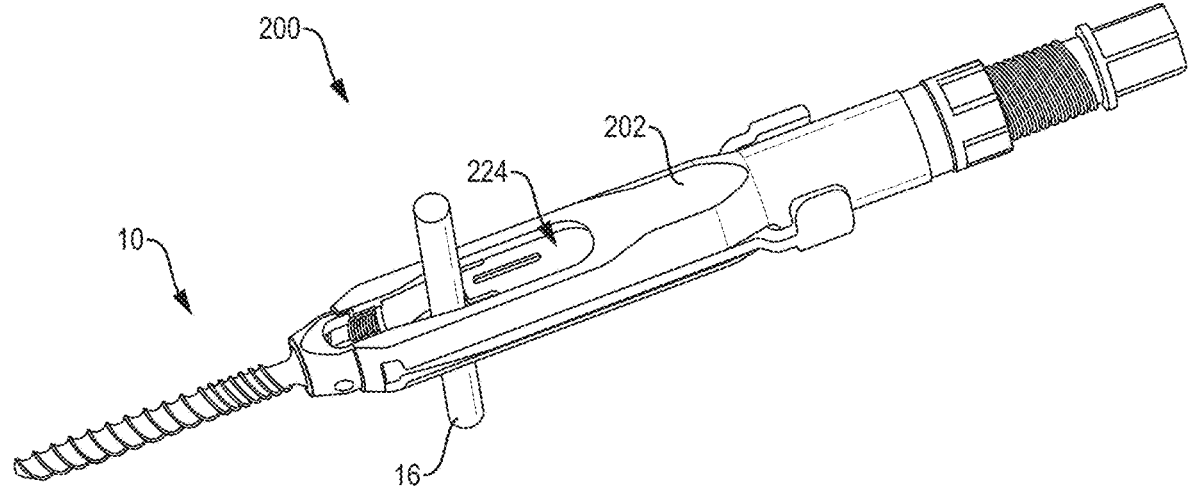
FIG. 34 is a perspective view of the reducer instrument of FIG. 32 docked to a bone anchor and reducing a spinal rod reduction.

FIG. 34 illustrates the reducer instrument 200 docked to a bone anchor 10 and reducing a spinal fixation rod 16. The arms 212a, 212b can engage the bone anchor 10, and the spinal rod 16 can be positioned transversely through the outer sleeve 202 between the arms 212a, 212b and distal to the static arms 234a, 234b of the inner sleeve 204 such that distal advancement of the inner sleeve 204 translates the static arms 234a, 234b distally into contact with the spinal rod 16. Further distal advancement translates the inner sleeve 204 through the outer sleeve 202 to force the spinal rod distally towards the bone anchor until the spinal rod is reduced into a rod seat of a receiver member of the bone anchor 10.

Figure 35:
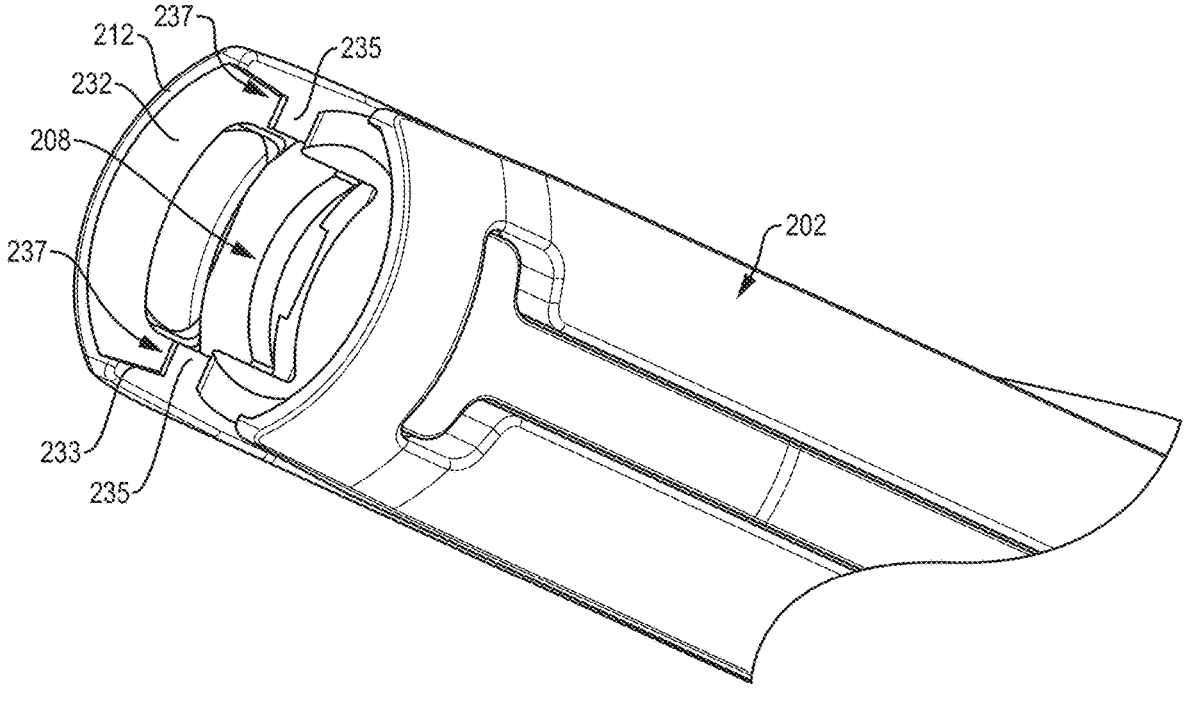
FIG. 35 is a detail perspective view of the distal end of the outer sleeve of the reducer instrument of FIG. 32.

In some instances, a reducer instrument can undesirably disengage from a bone anchor, for example, as a result of arms 212a, 212b splaying outward when the reducer instrument is subjected to certain loading conditions during use. In some embodiments, a distal portion of the arms 212a, 212b can have an increased thickness, resulting in an increased outer diameter being carried farther toward the distal end of the arms 212a, 212b. This can increase a stiffness and strength of the arms, which can help to combat unintentional arm splaying and possible decoupling from a bone anchor during use. Alternatively or in addition, the sidewalls 233 extending from the inner surfaces 232 of each arm 212 can include one or more extensions 235 that protrude medially into the channel 208 and distal pocket 231. Each extension 235 can form notch 237 between the extension and the inner surface 232, and the notch can be configured to receive a portion of a bone anchor therein. FIG. 35 shows the extensions 235 can be formed on opposite sides of each arm 212. The creation of the notch 237 provides a plurality of points of contact between the arms 212 and a bone anchor engaged therewith.

Figure 36:
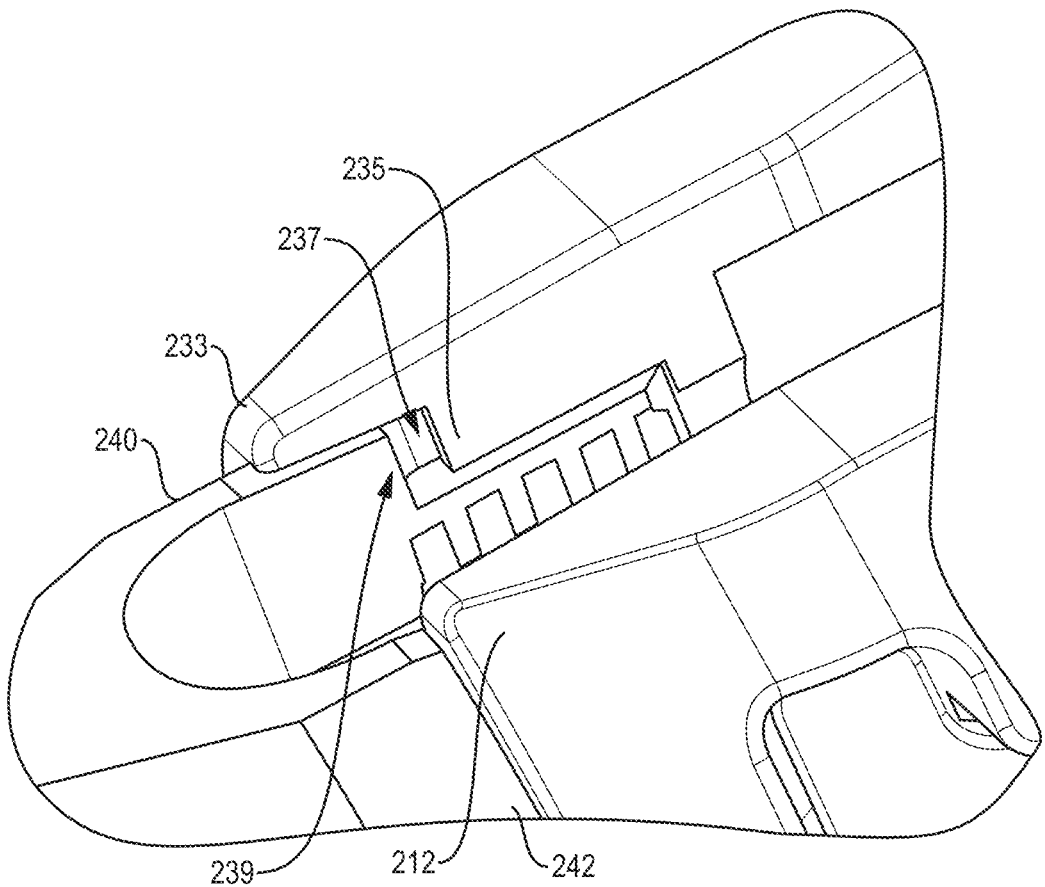
FIG. 36 is a detail perspective view of the reducer instrument of FIG. 34 coupled to a bone anchor

FIGS. 36-40 illustrate the interaction of the notches 237 with a bone anchor receiver member during coupling of the reducer instrument 200 to the bone anchor. As shown in the detail perspective view of FIG. 36, a proximal portion of the bone anchor receiver member 240 can be received within the notch 237 created between the inner surface 232 and the extension 235 of the arm 212. Since splaying forces urge the arm 212 radially outward relative to the bone anchor receiver member 240, the extension 235 disposed radially inward of one of the opposed arms 242 of the bone anchor receiver member can effectively resist any relative movement between the outer sleeve arm 212 and the receiver member 240. The bone anchor receiver member 240 can include one or more notches 239 formed at lateral ends of its opposed arms 242 that can be configured to receive the extension 235 without reducing a width of a rod slot opening between the opposed arms 242 of the receiver member 240. When disposed as shown in FIG. 36, the reducer instrument 200 can withstand high loads in different directions, such as those that occur during spinal rod reduction, without decoupling from the bone anchor 10 because the extension 235 abuts the sidewalls of the corresponding bone anchor notch 239 to prevent splaying of the arm 212.

Figure 37:
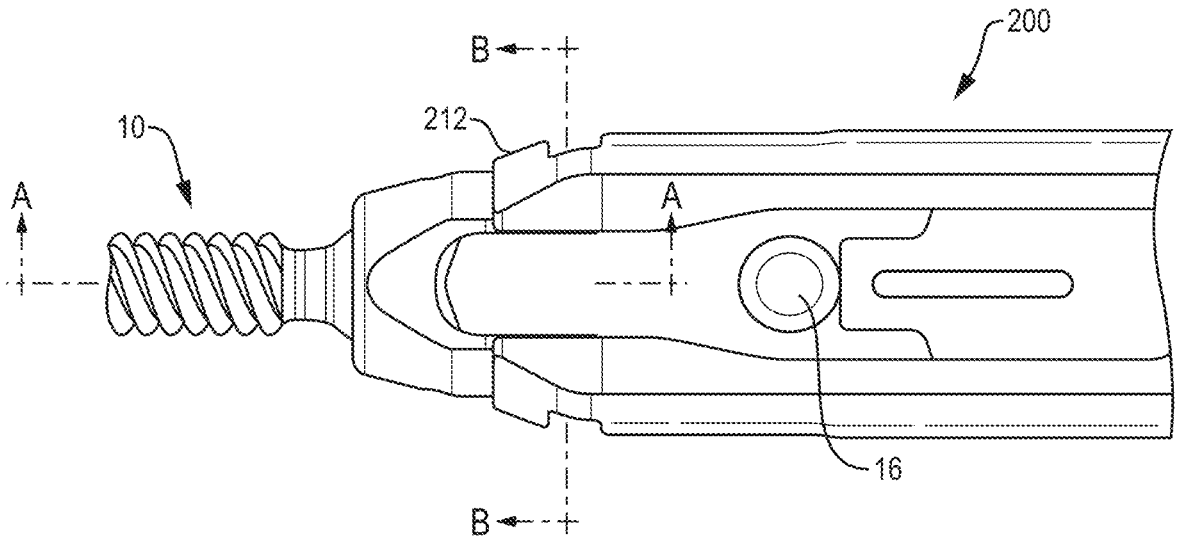
FIG. 37 is a detail side view of the reducer instrument of FIG. 32 docked to a bone anchor and reducing a spinal rod.

FIG. 37 illustrates a side view of the reducer instrument 200 coupled to a bone anchor 10 and reducing a spinal fixation rod 16. As shown in this figure, the outer sleeve 202 includes a rod capture opening 224 between the arms 212a, 212b that has a larger width along a proximal portion thereof and tapers to a narrower width distally. This configuration can permit greater tolerance for rotational and/or lateral misalignment of the rod and reducer instrument that can be gradually corrected as the rod is axially reduced toward a bone anchor. In some embodiments, the transition between the larger and narrower rod capture opening widths can be gradual or smooth to prevent the rod from binding against a more abrupt transition (e.g., a step or a small-diameter curved transition).

Figure 38:
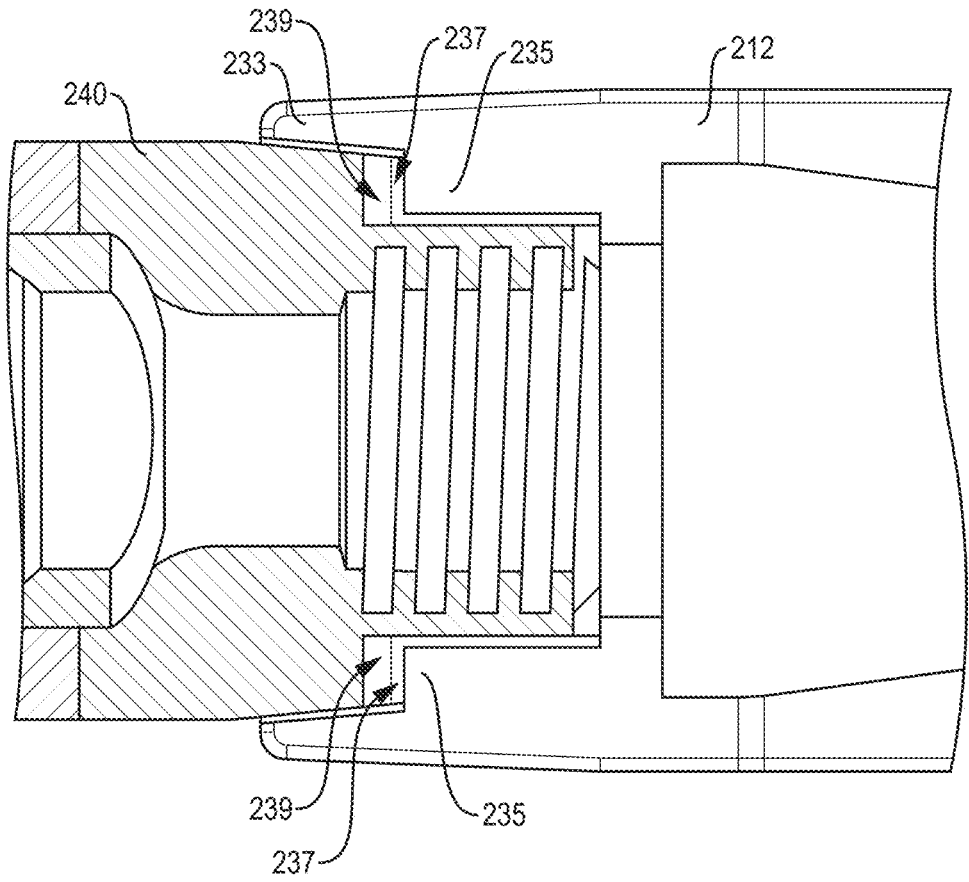
FIG. 38 is a side cross-sectional view of the reducer instrument of FIG. 37 taken along the line A-A.

FIG. 38 illustrates a cross-sectional view of the reducer instrument 200 and bone anchor 10 taken along the line A-A in FIG. 37. Similar to FIG. 36, the extensions 235 can be seen disposed in the notches 239 formed in the lateral edges of the bone anchor receiver member 240, which in turn means that the opposed arm of the receiver member 240 is disposed in the notches 237 formed between the extensions 235 and the inner surface 232 (obstructed in this view) of the arm 212. This creates a backstop whereby the extensions 235 can resist forces that would pull the arm 212 radially away (into the plane of the page in this view) from the receiver member 240.

Figure 39:
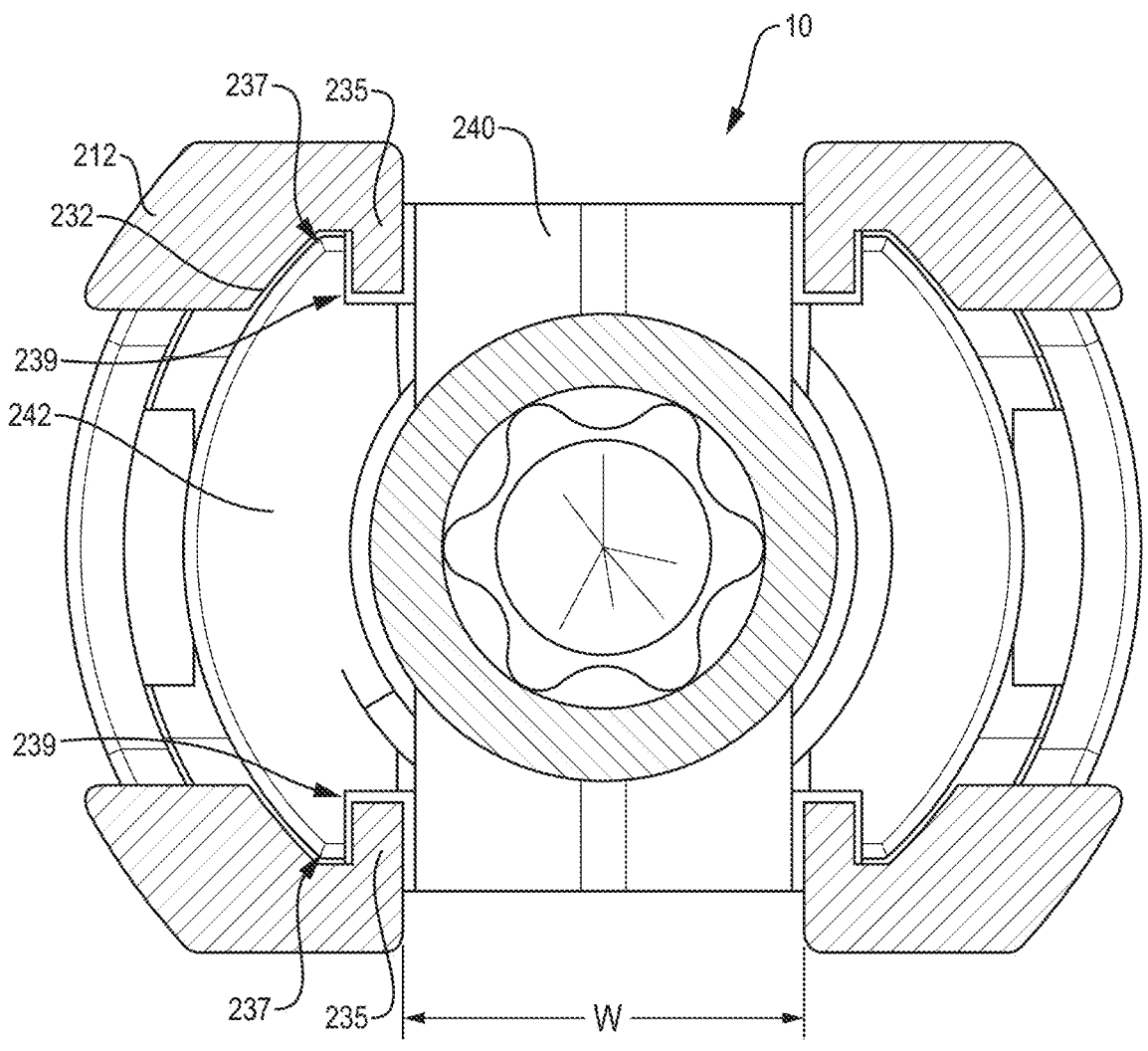
FIG. 39 is a distal-facing, transverse cross-sectional view of the reducer instrument of FIG. 37 taken along the line B-B.

FIG. 39 illustrates a cross-sectional view of the reducer instrument 200 and bone anchor 10 taken along the line B-B in FIG. 37. Similar to FIGS. 36 and 38, the configuration of the extensions 235 to create notches 237 between the inner surface 232 of the arm 212 and the extensions themselves is shown. Also show is the portion of the bone anchor receiver member arm 242 disposed within the notches 237 such that the extensions 235 can resist any radially outward forces (to the left and right in the plane of the page in this view) that might threaten to decouple the arms 212 from the receiver member opposed arms 242. Finally, the figure also shows that the extensions 235 are housed in notches 239 formed in the opposed arms 242 of the receiver member 240 such that a width W of the rod slot is not reduced. The configuration is repeated at each lateral edge of each arm 212.

Figure 40:
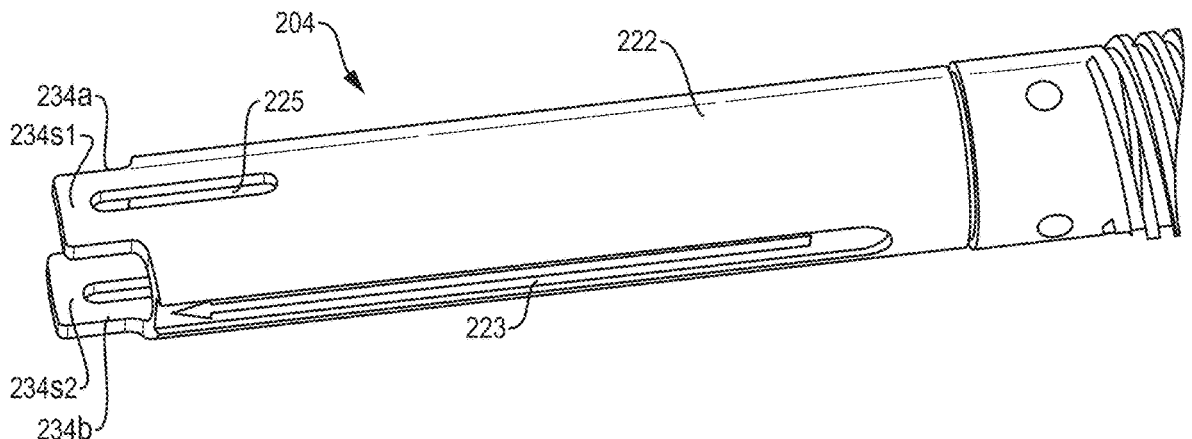
FIG. 40 is a perspective view of the inner sleeve of the reducer instrument of FIG. 32.
Figure 41:
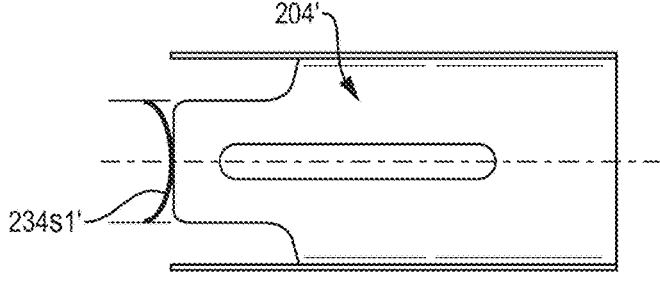
FIG. 41 is a side view of one embodiment of an inner sleeve having concave distal surfaces.

As discussed above with respect to FIG. 5, the distal translating member 222 can include first and second static or fixed arms 234a, 234b extending distally therefrom for performing rod reduction. For example, the arms 234a, 234b can contact and bear against a spinal rod to urge the rod distally as the inner sleeve 204 is translated distally within the reducer instrument 200. The arms 234 can include distal contact surfaces 234s1, 234s2 that can be configured to abut and/or otherwise engage the spinal rod during reduction of the reducer instrument 200 to advance the spinal rod distally into the bone anchor 10. As shown, the translating member 222 can taper distally towards substantially flat distal contact surfaces 234s1, 234s2, as shown in FIG. 40. In some embodiments, however, other distal contact surface shapes can be utilized. For example, in some embodiments the distal contact surfaces 234s1, 234s2 of the arms 234a, 234b can be shaped to match a rod shape with which the inner sleeve 204 is to be used. As shown in FIG. 41, for example, the arms 234a, 234b can include contact surfaces 234s1', 234s2' (not shown in the side view of the figure) that are concave in shape and have a diameter commensurate with the rod diameter.

Figure 42:
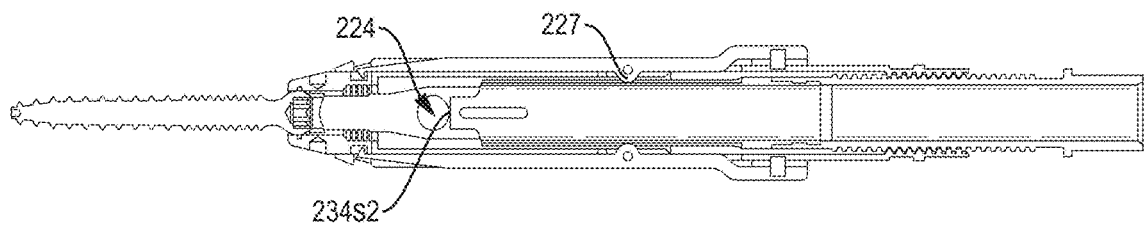
FIG. 42 is a side cross-sectional view of the reducer instrument and bone anchor of FIG. 34.

As noted above with respect to FIG. 34, the translating member 222 can be configured to advance distally without rotating to advance the spinal rod into the receiver member 240. To prevent unwanted rotation of the inner sleeve 204 with respect to the outer sleeve 202, a longitudinal groove 223 formed within the translating member 222 (see FIG. 40) can mate with a cam-like semi-circular surface or nub 227 on the underside of the lever fulcrum to prevent rotation of the translating member during reduction, as shown in FIG. 42. The nub 227 can extend from a surface of the arm 206 through an open recess and ride in the longitudinal groove 223 to permit translation while preventing rotation of the translating member 222 relative to the outer sleeve 202.

FIGS. 43-45 illustrate an alternate embodiment of a reducer instrument 200'. The reducer instrument 200' can include an alternate design of the pivoting arms 206a', 206b' without the nub 227. As shown in FIG. 44, which illustrates the reducer instrument 200' without the outer sleeve 202', the fulcrum 227' of the pivoting arms 206a', 206b' is flattened as compared to the nub 227 of the reducer instrument 100. Moreover, as shown in FIG. 45, the pivoting arms 206' of the reducer instrument 200' do not extend into the channel 223' of the inner sleeve 204'. To prevent rotation of the inner sleeve 204', the reducer instrument 200' includes one or more pins 242' disposed in one or more bores formed in the outer sleeve 202' such that pins extend into the channel 223' of the inner sleeve 204'. The one or more pins can be disposed proximal or distal to the fulcrum 227' at a position distal to the threads formed in the outer sleeve 202' such that they can be received within the groove 223' without interfering with threaded coupling between the outer sleeve and the inner sleeve 204' More particularly, the one or more pins 242' can ride within the key or groove 223' formed in the translating member 222' of the inner sleeve 204', as shown in FIG. 44, to prevent rotation of the translating member 222' relative to the outer sleeve 202'. In use, such as during docking of the reducer instrument 200' to a bone anchor 10, the pivoting arms 206a', 206b' can flex outward when passing over the receiver member 240 and flex inward to engage a notch or other feature formed in an outer surface of the receiver member 240.

FIG. 46 illustrates an alternate embodiment of an inner sleeve 304. The inner sleeve 304 can include a threaded member 320, a translating member 322, and a washer 324, e.g., a thrust washer that can separate and serve as a bearing surface between the translating member 322 and threaded member 320. As shown, the inner sleeve 304 can include an integrated handle 326 at a proximal end of the threaded member 320. The handle 326 can be integrally formed with the threaded member 320 to provide a unitary structure. The handle 326 can be configured to be grasped by a user to rotate the threaded member 320. In this manner, the integrated handle 326 can be a substitute for the modular drive feature (e.g., flats, hex drive feature, etc.) of the reducer instruments 100, 200 to allow direct manipulation of the inner sleeve without the need for any additional instrumentation. As noted above, any of a variety of handle configurations or other structures can be coupled with the threaded member in any of a variety of modular or permanent manners. These can include use of modular coupling features, such as the hex-drive feature 402, integrally formed structures, such as the integrated handle 326 and threaded member 320, and other coupling methods such as joining components with a set screw or other mechanical fastener, adhering components, welding components, etc.

In addition, the handle 326 can include a lumen 328 extending therethrough to allow introduction of a set screw or other instrument to a bone anchor coupled to a reducer instrument. The lumen 328 can extend through the integrated handle 326 and threaded member 320. In embodiments where a modular handle is utilized, it can include a lumen as well that, when coupled to the threaded member, can align with a lumen of the threaded member to permit introduction of a set screw or other instrument therethrough. Accordingly, the methods described above (e.g., in connection with FIGS. 18-21) can be utilized with embodiments including both a modularly-coupled handle and an integrally-formed and/or permanently coupled handle.

The instruments disclosed herein can be constructed from any of a variety of known materials. Example materials include those which are suitable for use in surgical applications, including metals such as stainless steel, titanium, nickel, cobalt-chromium, or alloys and combinations thereof, polymers such as PEEK, ceramics, carbon fiber, and so forth. Further, various methods of manufacturing can be utilized, including 3D printing or other additive manufacturing techniques, as well as more conventional manufacturing techniques, including molding, stamping, casting, machining, etc.

The devices and methods disclosed herein can be used in minimally-invasive surgery and/or open surgery. While the devices and methods disclosed herein are generally described in the context of surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly, followed by cleaning or replacement of particular pieces, and subsequent reassembly. In particular, the device or component can be disassembled, and any number of the particular pieces or parts thereof can be selectively replaced or removed in any combination. Upon cleaning and/or replacement of particular parts, the device or component can be reassembled for subsequent use either at a reconditioning facility, or by a surgical team immediately prior to a surgical procedure. Reconditioning of a device or component can utilize a variety of techniques for disassembly, cleaning/replacement, and reassembly. Use of such techniques, and the resulting reconditioned device, are all within the scope of the present application.

The devices described herein can be processed before use in a surgical procedure. For example, a new or used instrument or component can be obtained and, if necessary, cleaned. The instrument or component can be sterilized. In one sterilization technique, the instrument or component can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument or component and in the container. The sterilized instrument or component can then be stored in the sterile container. The sealed container can keep the instrument or component sterile until it is opened in the medical facility. Other forms of sterilization are also possible, including beta or other forms of radiation, ethylene oxide, steam, or a liquid bath (e.g., cold soak). Certain forms of sterilization may be better suited to use with different portions of the device due to the materials utilized, the presence of electrical components, etc.

In this disclosure, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B," "one or more of A and B," and "A and/or B" are each intended to mean "A alone, B alone, or A and B together." A similar interpretation is also intended for lists including three or more items. For example, the phrases "at least one of A, B, and C," "one or more of A, B, and C," and "A, B, and/or C" are each intended to mean "A alone, B alone, C alone, A and B together, A and C together, B and C together, or A and B and C together." In addition, use of the term "based on," is intended to mean, "based at least in part on," such that an un-recited feature or element is also permissible.

Further features and advantages based on the above-described embodiments are possible and within the scope of the present disclosure. Accordingly, the disclosure is not to be limited by what has been particularly shown and described. All publications and references cited herein are incorporated by reference in the entirety, except for any definitions, subject matter disclaimers, or disavowals, and except to the extent that the incorporated material is inconsistent with the express disclosure herein, in which case the language in this disclosure controls.

Examples of the above-described embodiments can include the following:

1. A surgical instrument, comprising:
   an outer sleeve having an inner channel defined therein, the outer sleeve terminating in a pair of extensions at a distal end thereof;
   an inner sleeve having a proximal threaded portion and a distal translating portion configured to pass through the outer sleeve; and
   a pair of pivoting arms received in the extensions in the outer sleeve, the pivoting arms being configured to extend into the channel to couple a bone anchor to the outer sleeve;
   wherein a proximal end portion of the outer sleeve includes one or more flats configured to engage with another instrument.

2. The instrument of example 1, wherein the pivoting arms are spring-loaded to bias to a closed position.

3. The instrument of any of examples 1 to 2, wherein the threaded portion includes a first threaded portion and a second threaded portion separated by a non-threaded portion.

4. The instrument of any of examples 1 to 3, wherein the threaded portion is configured to be pulled and rotated to be removed from the outer sleeve.

5. The instrument of any of examples 1 to 4, wherein the proximal end portion of the outer sleeve includes a circumferential groove.

6. The instrument of any of examples 1 to 5, wherein the pair of pivoting arms further comprises a nub that extends into one or more longitudinal grooves of the distal translating portion of the inner sleeve to prevent rotation of the distal translating portion relative to the outer sleeve.

7. The instrument of any of examples 1 to 5, further comprising a pin that extends into one or more longitudinal grooves of the distal translating portion of the inner sleeve to prevent rotation of the distal translating portion.

8. The instrument of any of examples 1 to 7, further comprising a counter-torque device having a mating feature that corresponds to the one or more flats on the outer sleeve.

9. The instrument of any of examples 1 to 8, further comprising a derotation sleeve that defines a lumen therethrough, the derotation sleeve being configured to couple to the outer sleeve, the derotation sleeve having one or more engagement surfaces that overlap with the one or more flats to facilitate coupling.

10. The instrument of example 9, wherein the derotation sleeve further comprises a pair of hinged arms that are configured to extend into the lumen to further couple the derotation sleeve to the outer sleeve.

11. The instrument of example 10, wherein the derotation sleeve further comprises a locking ring configured to selectively constrain movement of the hinged arms.

12. The instrument of example 10, wherein the hinged arms are received in a circumferential groove along the outer sleeve.

13. A surgical instrument, comprising:
a housing having a central opening, a proximal end, a distal end, and a central longitudinal axis (A1) extending between the proximal and distal ends;
first and second fixed arms extending distally from the housing;
first and second pivoting arms movably coupled to the housing, each pivoting arm having a proximal end and a distal end, the pivoting arms being configured to selectively retain a bone anchor therebetween; and
a reducer shaft threadably mounted in the central opening of the housing;
wherein each of the first and second arms extending distally from the housing define an inner surface and each of the first and second arms includes sidewalls extending outward from the inner surface at lateral ends of each arm.

14. The instrument of example 13, wherein the inner surface of each of the first and second arms has a conical tapering profile.

15. The instrument of any of examples 13 to 14, wherein opposed, inward-facing surfaces of each sidewall of an arm have a planar tapering profile.

16. The instrument of any of examples 13 to 15, wherein the pivoting arms are mounted in recesses formed in the fixed arms.

17. The instrument of any of examples 13 to 16, wherein the pivoting arms are pivotably coupled to the housing at a location intermediate the proximal and distal ends of the pivoting arms.

18. The instrument of any of examples 13 to 17, wherein the reducer shaft comprises a first portion having an exterior thread and being configured to rotate relative to the housing to advance the reducer shaft distally relative to the housing.

19. The instrument of example 18, wherein the reducer shaft comprises a second portion that is rotationally-fixed relative to the housing, the second portion comprising a distal-facing rod-engaging surface.

20. The instrument of example 19, wherein the first portion includes one or more inwardly-facing projections received within a circumferential groove formed in an exterior surface of the second portion.

21. The instrument of any of examples 13 to 20, wherein the reducer shaft defines a working channel extending therethrough.

22. The instrument of any of examples 13 to 21, wherein a distal end portion of the reducer shaft includes a visualization window formed therein.

23. The instrument of any of examples 13 to 22, wherein the reducer shaft comprises a drive interface at a proximal end of the reducer shaft.

24. The instrument of any of examples 13 to 23, wherein the reducer shaft comprises a handle at a proximal end thereof that is configured to be grasped by a user.

25. The instrument of any of examples 13 to 24, further comprising a derotation shaft selectively attachable to the reducer shaft.

26. The instrument of example 25, wherein the derotation shaft comprises an elongate body defining a working channel extending therethrough, the working channel of the derotation shaft being in communication with a working channel of the reducer shaft and the central opening of the housing.

27. The instrument of example 25, wherein the derotation shaft includes opposed hinged arms and a locking ring, wherein the locking ring is movable between a locked position, in which the locking ring maintains the hinged arms in a radially inward position where they engage a groove formed in the housing, and an unlocked position, in which the hinged arms can move radially outward to disengage from the groove of the housing.

28. The instrument of example 25, wherein the derotation shaft comprises a drive interface at a proximal end of the derotation shaft.

29. The instrument of any of examples 13 to 28, wherein the sidewalls include extensions that form a notch between each extension and the inner surface.

30. The instrument of example 29, wherein the notch is configured to receive a portion of a bone anchor.

31. The instrument of any of examples 13 to 30, wherein the reducer shaft includes a substantially flat distal surface configured to engage a spinal rod.

32. The instrument of any of examples 13 to 30, wherein the reducer shaft includes a concave distal surface configured to engage a spinal rod.

What is claimed is:

1. A surgical assembly, comprising:
a unitary outer sleeve defined by a tubular central portion extending from a proximal end to a distal end and having a sidewall that circumscribes an inner channel, the proximal end having one or more flats oriented around a circumference thereof, and the distal end terminating in a pair of extensions configured to receive a bone anchor therebetween;

an inner sleeve having a proximal threaded portion and a distal translating portion configured to pass through the inner channel of the outer sleeve; and a pair of pivoting arms received in the outer sleeve, the pair of pivoting arms each extending from a proximal end having an actuator formed thereon to a distal end that is configured to extend into the inner channel to couple the outer sleeve to the bone anchor.

2. The assembly of claim 1, wherein the outer sleeve further comprises a circumferential groove that extends around a circumference of the outer sleeve to facilitate engagement of one or more instruments to the sidewall of the outer sleeve.

3. The assembly of claim 2, wherein the circumferential groove is distal to the one or more flats.

4. The assembly of claim 1, wherein the inner channel comprises one or more mating features having a threaded inner surface configured to cooperate with one or more instruments disposed within the inner channel.

5. The assembly of claim 1, further comprising a counter-torque device having a mating feature that corresponds to the one or more flats for coupling thereto.

6. The assembly of claim 1, wherein the pivoting arms are spring-loaded to bias to a closed position wherein the distal ends of the pivoting arms extend into the inner channel.

7. The assembly of claim 1, wherein the outer sleeve further comprises a pair of opposed longitudinal recesses configured to receive a portion of the pair of pivoting arms therein.

8. The assembly of claim 7, wherein the distal end of each pivoting arm is received in one of the opposed longitudinal recesses and the proximal end of each pivoting arm is disposed outside of the outer sleeve.

9. The assembly of claim 7, wherein an inner surface of the proximal end of each pivoting arm is disposed outside of the outer sleeve.

10. The assembly of claim 9, wherein the inner surface of the proximal end of each pivoting arm is positioned proximally to the pair of opposed longitudinal recesses.

11. The assembly of claim 1, wherein the distal translating portion further comprises one or more longitudinal grooves that extend along a length thereof.

12. The assembly of claim 11, wherein at least one pivoting arm includes a protrusion that is configured to extend into the one or more longitudinal grooves of the distal translating portion of the inner sleeve to mate thereto.

13. The assembly of claim 1, wherein the one or more flats are recessed relative to an outer surface of the sidewall.

14. A surgical assembly, comprising:

an outer sleeve defined by a tubular central portion extending from a proximal end to a distal end and having a sidewall that circumscribes an inner channel, the proximal end having one or more flats oriented around a circumference thereof, and the distal end terminating in a pair of extensions configured to receive a bone anchor therebetween;

an inner sleeve having a proximal threaded portion and a distal translating portion configured to pass through the inner channel of the outer sleeve; and a pair of pivoting arms received in the outer sleeve, the pair of pivoting arms each extending from a proximal end having an actuator formed thereon to a distal end that is configured to extend into the inner channel to couple the outer sleeve to the bone anchor;

wherein the outer sleeve further comprises a circumferential groove that extends around a circumference of the outer sleeve to facilitate engagement of one or more instruments to the sidewall of the outer sleeve.

15. The assembly of claim 14, wherein the circumferential groove is distal to the one or more flats.

16. The assembly of claim 14, wherein the inner channel comprises one or more mating features having a threaded inner surface configured to cooperate with one or more instruments disposed within the inner channel.

17. The assembly of claim 14, wherein the one or more flats are recessed relative to an outer surface of the sidewall.

18. A surgical assembly, comprising:

an outer sleeve defined by a tubular central portion extending from a proximal end to a distal end and having a sidewall that circumscribes an inner channel, the proximal end having one or more flats oriented around a circumference thereof, and the distal end terminating in a pair of extensions configured to receive a bone anchor therebetween;

an inner sleeve having a proximal threaded portion and a distal translating portion configured to pass through the inner channel of the outer sleeve; and a pair of pivoting arms received in the outer sleeve, the pair of pivoting arms each extending from a proximal end having an actuator formed thereon to a distal end that is configured to extend into the inner channel to couple the outer sleeve to the bone anchor;

wherein the one or more flats are recessed relative to an outer surface of the sidewall.

19. The assembly of claim 18, wherein the outer sleeve further comprises a circumferential groove that extends around a circumference of the outer sleeve to facilitate engagement of one or more instruments to the sidewall of the outer sleeve.

20. The assembly of claim 19, wherein the circumferential groove is distal to the one or more flats.

21. The assembly of claim 18, wherein the inner channel comprises one or more mating features having a threaded inner surface configured to cooperate with one or more instruments disposed within the inner channel.

* * * * *